(12) United States Patent
Khosrovaninejad

(10) Patent No.: US 12,733,932 B2
(45) **Date of Patent: *Sep. 15, 2026**

(54) SURGICAL DEVICE FOR CONTROLLED ANCHORING IN THE INTESTINE

(71) Applicant: Charam Khosrovaninejad, Pernes les Fontaines (FR)

(72) Inventor: Charam Khosrovaninejad, Pernes les Fontaines (FR)

( * ) Notice: Subject to any disclaimer, the term of this patent is extended or adjusted under 35 U.S.C. 154(b) by 0 days.

This patent is subject to a terminal disclaimer.

(21) Appl. No.: 19/540,471

(22) Filed: Feb. 13, 2026

(65) Prior Publication Data

US 2026/0174435 A1 Jun. 25, 2026

Related U.S. Application Data

(60) Continuation of application No. 19/330,687, filed on Sep. 16, 2025, now Pat. No. 12,558,095, which is a (Continued)

(30) Foreign Application Priority Data

Jul. 25, 2011 (FR) ...................................... 1156771

(51) Int. Cl.
*A61F 2/04* (2013.01)
*A61B 17/08* (2006.01)
(Continued)

(52) U.S. Cl.
CPC ................ *A61B 17/08* (2013.01); *A61F 2/04* (2013.01); *A61F 5/0013* (2013.01); (Continued)

(58) Field of Classification Search
CPC ....... A61B 17/1114; A61B 2017/00818; A61F 2/04; A61F 2/064; A61F 2/07; A61F 2/82;
(Continued)

(56) References Cited

U.S. PATENT DOCUMENTS 2,821,190 A 1/1958 Chase
3,799,172 A 3/1974 Szpur
(Continued)

FOREIGN PATENT DOCUMENTS

CN 102387759 A 3/2012
CN 103370016 A 10/2013
(Continued)

OTHER PUBLICATIONS

Buhl S., et al., "Humidity Influence on the Adhesion of Biomimetic Fibrillar Surfaces", International Journal of Materials Research, 2009, vol. 100, No. 8, pp. 1119-1126.
(Continued)

*Primary Examiner* — Diane D Yabut
(74) *Attorney, Agent, or Firm* — Greenberg Traurig, LLP; Christopher C. Bolten; Albert K. Heng

(57) ABSTRACT

A surgical anchor device for being anchored on the mucous membrane of the inner wall of the intestine, the device having a temporary anchor element presenting anchoring that can be modified in a controlled manner and having a first substantially cylindrical multiply-perforated wall presenting properties of radial elasticity whereby the first wall presents an outer diameter that can be varied in controlled manner, wherein a portion of the inner surface of the first wall is lined with an independent leakproof inner sheath having only its longitudinal ends fastened to the anchor element to define a suction chamber between the inner sheath and the first wall, the temporary anchor element being coupled to a flexible or semi-rigid tube extending outside the anchor element, an open end of the injection-suction tube opening out into the suction chamber enabling air to be injected into or sucked out from the suction chamber.

25 Claims, 4 Drawing Sheets

Related U.S. Application Data continuation of application No. 19/210,993, filed on May 16, 2025, now Pat. No. 12,433,592, which is a continuation of application No. 18/940,115, filed on Nov. 7, 2024, now Pat. No. 12,324,584, which is a continuation of application No. 18/770,634, filed on Jul. 11, 2024, now Pat. No. 12,137,911, which is a continuation of application No. 18/333,101, filed on Jun. 12, 2023, now Pat. No. 12,042,148, which is a continuation of application No. 18/312,335, filed on May 4, 2023, now Pat. No. 12,048,433, which is a continuation of application No. 17/071,034, filed on Oct. 15, 2020, now Pat. No. 11,857,191, which is a division of application No. 15/959,553, filed on Apr. 23, 2018, now Pat. No. 10,835,248, which is a division of application No. 14/234,834, filed as application No. PCT/FR2012/051576 on Jul. 5, 2012, now Pat. No. 9,980,727.

(51) Int. Cl.

*A61B 17/11* (2006.01)
*A61F 5/00* (2006.01)
*A61B 17/00* (2006.01)
*A61B 17/30* (2006.01)
*A61B 90/00* (2016.01)
*A61F 2/06* (2013.01)
*A61F 2/07* (2013.01)
*A61F 2/95* (2013.01)

(52) U.S. Cl.

CPC .......... *A61F 5/0076* (2013.01); *A61F 5/0089* (2013.01); *A61B 2017/00818* (2013.01); *A61B 2017/00862* (2013.01); *A61B 2017/00995* (2013.01); *A61B 17/1114* (2013.01); *A61B 2017/308* (2013.01); *A61B 2090/0815* (2016.02); *A61F 2002/044* (2013.01); *A61F 2002/045* (2013.01); *A61F 2/064* (2013.01); *A61F 2002/075* (2013.01); *A61F 2/95* (2013.01); *A61F 2002/9528* (2013.01); *F04C 2270/041* (2013.01)

(58) Field of Classification Search

CPC .... A61F 2/852; A61F 2/86; A61F 2/95; A61F 5/0003; A61F 5/0013; A61F 5/0076; A61F 5/0089; A61F 2002/044; A61F 2002/045; A61F 2002/075

See application file for complete search history.

(56) References Cited

U.S. PATENT DOCUMENTS 3,885,567 A 5/1975 Ross
4,627,837 A 12/1986 Gonzalo
4,716,900 A 1/1988 Ravo et al.
4,721,109 A 1/1988 Healey
5,358,496 A 10/1994 Ortiz et al.
5,425,739 A 6/1995 Jessen
5,534,007 A 7/1996 St. Germain et al.
5,558,642 A 9/1996 Schweich, Jr. et al.
5,594,038 A 1/1997 Kobayashi et al.
5,846,251 A 12/1998 Hart
5,876,448 A 3/1999 Thompson et al.
6,068,636 A 5/2000 Chen
6,103,255 A 8/2000 Levene et al.
6,146,416 A 11/2000 Andersen et al.
6,254,642 B1 7/2001 Taylor
6,325,798 B1 12/2001 Edwards et al.
6,379,379 B1 4/2002 Wang
6,398,758 B1 6/2002 Jacobsen et al.
6,514,282 B1 2/2003 Inoue
6,585,926 B1 7/2003 Mirzaee
6,733,519 B2 5/2004 Lashinski et al.
6,808,492 B2 10/2004 Snyder
6,926,724 B1 8/2005 Chu
7,025,791 B2 4/2006 Levine et al.
7,147,627 B2 12/2006 Kim et al.
7,267,694 B2 9/2007 Levine et al.
7,267,794 B2 9/2007 Amick
7,316,716 B2 1/2008 Egan
7,347,875 B2 3/2008 Levine et al.
7,509,175 B2 3/2009 Sparks et al.
7,547,312 B2 6/2009 Bauman et al.
7,631,153 B2 12/2009 Mahrla et al.
7,643,887 B2 1/2010 Imran
7,678,090 B2 3/2010 Risk, Jr. et al.
7,744,914 B2 6/2010 Li et al.
7,766,973 B2 8/2010 Levine et al.
7,776,081 B2 8/2010 Zuidema et al.
7,815,591 B2 10/2010 Levine et al.
8,007,541 B2 8/2011 Benz et al.
8,083,758 B2 12/2011 Hsu et al.
8,114,045 B2 2/2012 Surti
8,118,774 B2 2/2012 Dann et al.
8,167,859 B2 5/2012 Shah et al.
8,182,527 B2 5/2012 Llanos et al.
8,187,254 B2 5/2012 Hissink et al.
8,211,186 B2 7/2012 Belhe et al.
8,221,783 B2 7/2012 Helmus et al.
8,282,598 B2 10/2012 Belhe et al.
8,323,229 B2 12/2012 Shin et al.
8,376,981 B2 2/2013 Laufer
8,398,669 B2 3/2013 Kim
8,435,283 B2 5/2013 Jordan et al.
8,491,612 B2 7/2013 Stopek et al.
8,597,224 B2 12/2013 Vargas
8,636,810 B2 1/2014 Rousseau
8,690,817 B2 4/2014 Assaf et al.
8,702,641 B2 4/2014 Belhe et al.
8,702,642 B2 4/2014 Belhe et al.
8,709,093 B2 4/2014 Robida et al.
8,753,407 B2 6/2014 Nguyen
8,801,647 B2 8/2014 Melanson et al.
8,821,429 B2 9/2014 Vargas
8,828,090 B2 9/2014 Terliuc
8,894,699 B2 11/2014 Kelley
8,900,268 B2 12/2014 Weidenhagen et al.
8,906,046 B2 12/2014 Anderson
8,926,593 B2 1/2015 Croizat et al.
9,044,300 B2 6/2015 Belhe et al.
9,173,734 B2 11/2015 Vargas
9,265,640 B2 2/2016 Harris et al.
9,339,272 B2 5/2016 Khosrovaninejad
9,398,982 B2 7/2016 Kleiner
9,402,630 B2 8/2016 Stopek et al.
9,439,790 B2 9/2016 Clerc et al.
9,511,208 B2 12/2016 Assaf et al.
9,517,122 B2 12/2016 Firstenberg et al.
9,526,640 B2 12/2016 Bertolino et al.
9,597,206 B2 3/2017 Seddon et al.
9,675,360 B2 6/2017 Baker
9,687,334 B2 6/2017 Williams et al.
9,750,596 B2 9/2017 Levine et al.
9,764,067 B2 9/2017 Fleury et al.
9,789,291 B2 10/2017 Assaf et al.
9,827,135 B2 11/2017 Fong et al.
9,980,727 B2 5/2018 Khosrovaninejad
10,058,413 B2 8/2018 Heiss
10,172,622 B2 1/2019 Kelley
10,271,972 B2 4/2019 Guler et al.
10,441,406 B2 10/2019 Firstenberg et al.
10,456,138 B2 10/2019 Khosrovaninejad
10,531,941 B2 1/2020 Hynes et al.
10,758,380 B2 9/2020 Bluecher et al.
10,779,928 B2 9/2020 Heiss
10,835,248 B2 11/2020 Khosrovaninejad
10,973,675 B2 4/2021 Fong et al.
11,406,486 B2 8/2022 Heiss
11,534,149 B2 12/2022 Assaf et al.
11,589,869 B2 2/2023 Khosrovaninejad et al.

(56) References Cited

U.S. PATENT DOCUMENTS

| | | | |
|---|---|---|---|
| 11,857,191 | B2 | 1/2024 | Khosrovaninejad |
| 11,871,929 | B2 | 1/2024 | Khosrovaninejad et al. |
| 11,903,865 | B2 | 2/2024 | Fong et al. |
| 12,042,148 | B2 | 7/2024 | Khosrovaninejad |
| 12,042,150 | B2 | 7/2024 | Khosrovaninejad et al. |
| 12,048,433 | B2 | 7/2024 | Khosrovaninejad |
| 12,059,368 | B2 | 8/2024 | Fong et al. |
| 12,137,911 | B1 | 11/2024 | Khosrovaninejad |
| 12,213,673 | B2 | 2/2025 | Augelli et al. |
| 12,239,321 | B2 | 3/2025 | Augelli et al. |
| 12,245,766 | B2 | 3/2025 | Augelli et al. |
| 12,324,584 | B2 | 6/2025 | Khosrovaninejad |
| 12,433,592 | B2 | 10/2025 | Khosrovaninejad et al. |
| 12,447,262 | B2 | 10/2025 | Leveau-Mollier |
| 12,478,377 | B2 | 11/2025 | Khosrovaninejad et al. |
| 2001/0037808 | A1 | 11/2001 | Deem et al. |
| 2002/0033226 | A1 | 3/2002 | Kohinata et al. |
| 2004/0044358 | A1 | 3/2004 | Khosravi et al. |
| 2004/0107004 | A1 | 6/2004 | Levine et al. |
| 2004/0122527 | A1 | 6/2004 | Imran |
| 2004/0147864 | A1 | 7/2004 | Lenker et al. |
| 2005/0004663 | A1 | 1/2005 | Llanos et al. |
| 2005/0033226 | A1 | 2/2005 | Kim |
| 2005/0062610 | A1 | 3/2005 | Johnson |
| 2005/0228409 | A1 | 10/2005 | Coppi |
| 2005/0255230 | A1 | 11/2005 | Clerc et al. |
| 2005/0256587 | A1 | 11/2005 | Egan |
| 2005/0273075 | A1 | 12/2005 | Krulevitch et al. |
| 2006/0064120 | A1 | 3/2006 | Levine et al. |
| 2006/0095124 | A1 | 5/2006 | Benz et al. |
| 2006/0112536 | A1 | 6/2006 | Herweck et al. |
| 2006/0141012 | A1 | 6/2006 | Gingras |
| 2006/0151568 | A1 | 7/2006 | Weller et al. |
| 2007/0032879 | A1 | 2/2007 | Levine et al. |
| 2007/0045229 | A1 | 3/2007 | Keenan et al. |
| 2007/0179590 | A1 | 8/2007 | Lu et al. |
| 2007/0262161 | A1 | 11/2007 | Davies |
| 2007/0282247 | A1 | 12/2007 | Desai et al. |
| 2007/0282452 | A1 | 12/2007 | Weitzner et al. |
| 2008/0004566 | A1 | 1/2008 | Sloan |
| 2008/0033244 | A1 | 2/2008 | Matsui et al. |
| 2008/0039878 | A1 | 2/2008 | Williams et al. |
| 2008/0161717 | A1 | 7/2008 | Gertner |
| 2008/0167606 | A1 | 7/2008 | Dann et al. |
| 2008/0195226 | A1 | 8/2008 | Williams et al. |
| 2008/0208325 | A1 | 8/2008 | Helmus et al. |
| 2008/0208357 | A1 | 8/2008 | Melanson et al. |
| 2008/0249504 | A1 | 10/2008 | Lattouf et al. |
| 2008/0255592 | A1 | 10/2008 | Hsu et al. |
| 2009/0018606 | A1 | 1/2009 | Sparks et al. |
| 2009/0069904 | A1 | 3/2009 | Picha |
| 2009/0143722 | A1 | 6/2009 | Kim |
| 2009/0143772 | A1 | 6/2009 | Kurtz |
| 2009/0220677 | A1 | 9/2009 | Clerc et al. |
| 2009/0276055 | A1 | 11/2009 | Harris et al. |
| 2010/0010519 | A1 | 1/2010 | Stopek et al. |
| 2010/0174381 | A1 | 7/2010 | Benz et al. |
| 2010/0179633 | A1 | 7/2010 | Solem |
| 2010/0282813 | A1 | 11/2010 | Milliman |
| 2011/0092950 | A1 | 4/2011 | Shachar et al. |
| 2011/0172760 | A1 | 7/2011 | Anderson |
| 2011/0202084 | A1 | 8/2011 | Hoem et al. |
| 2011/0295288 | A1 | 12/2011 | Khosrovaninejad |
| 2012/0095541 | A1 | 4/2012 | Kramann |
| 2012/0116528 | A1 | 5/2012 | Nguyen |
| 2013/0006382 | A1 | 1/2013 | Behan |
| 2013/0087579 | A1 | 4/2013 | Knighton |
| 2013/0087597 | A1 | 4/2013 | Shelton, IV et al. |
| 2013/0158463 | A1 | 6/2013 | Assaf et al. |
| 2013/0178879 | A1 | 7/2013 | Laufer |
| 2013/0218262 | A1 | 8/2013 | Ishii et al. |
| 2013/0231753 | A1 | 9/2013 | Liddy et al. |
| 2013/0274717 | A1 | 10/2013 | Dunn |
| 2013/0304101 | A1 | 11/2013 | Stopek et al. |
| 2014/0088622 | A1 | 3/2014 | Rousseau |
| 2014/0118029 | A1 | 5/2014 | Tseng et al. |
| 2014/0163664 | A1 | 6/2014 | Goldsmith |
| 2014/0222039 | A1 | 8/2014 | Khosrovaninejad |
| 2014/0350694 | A1 | 11/2014 | Behan |
| 2014/0371870 | A1 | 12/2014 | Terliuc |
| 2015/0045715 | A1 | 2/2015 | Assaf et al. |
| 2015/0119641 | A1 | 4/2015 | Yamada |
| 2015/0342760 | A1 | 12/2015 | Christakis et al. |
| 2016/0220256 | A1 | 8/2016 | Khosrovaninejad |
| 2016/0367352 | A1 | 12/2016 | Heiss |
| 2017/0027729 | A1 | 2/2017 | Abu Dayyeh |
| 2017/0071780 | A1 | 3/2017 | Fong et al. |
| 2017/0087343 | A1 | 3/2017 | Assaf et al. |
| 2017/0189217 | A1 | 7/2017 | Folan et al. |
| 2017/0265849 | A1 | 9/2017 | Assaf et al. |
| 2017/0333042 | A1 | 11/2017 | Sato |
| 2018/0070800 | A1 | 3/2018 | Yeung et al. |
| 2018/0071078 | A1 | 3/2018 | Majolagbe |
| 2018/0235631 | A1 | 8/2018 | Khosrovaninejad |
| 2020/0000329 | A1 | 1/2020 | Sugaya |
| 2020/0338808 | A1 | 10/2020 | Hulseman et al. |
| 2021/0001019 | A1 | 1/2021 | Elder et al. |
| 2021/0008336 | A1 | 1/2021 | Rajagopalan et al. |
| 2021/0038224 | A1 | 2/2021 | Khosrovaninejad |
| 2021/0145624 | A1 | 5/2021 | Fong et al. |
| 2021/0205065 | A1 | 7/2021 | Cote et al. |
| 2021/0315578 | A1 | 10/2021 | Khosrovaninejad et al. |
| 2022/0000345 | A1 | 1/2022 | Lalli et al. |
| 2022/0105320 | A1 | 4/2022 | Göbel |
| 2022/0151465 | A1 | 5/2022 | Johnsen et al. |
| 2022/0250254 | A1 | 8/2022 | Hulseman et al. |
| 2022/0355017 | A1 | 11/2022 | Depierro |
| 2022/0361880 | A2 | 11/2022 | Khosrovaninejad et al. |
| 2023/0083639 | A1 | 3/2023 | Caplan et al. |
| 2024/0058008 | A1 | 2/2024 | Morris et al. |
| 2024/0350295 | A1 | 10/2024 | Fong et al. |
| 2024/0407907 | A1 | 12/2024 | Heiss |
| 2025/0000683 | A1 | 1/2025 | Fong et al. |
| 2025/0041096 | A1 | 2/2025 | Fong et al. |
| 2025/0114232 | A1 | 4/2025 | Fong et al. |
| 2025/0275770 | A1 | 9/2025 | Khosrovaninejad |

FOREIGN PATENT DOCUMENTS

| | | | |
|---|---|---|---|
| CN | 103764069 | A | 4/2014 |
| CN | 204169953 | U | 2/2015 |
| CN | 108261577 | A | 7/2018 |
| EP | 1405612 | A1 | 4/2004 |
| EP | 2143389 | A1 | 1/2010 |
| EP | 2165665 | A1 | 3/2010 |
| EP | 2143388 | B1 | 6/2011 |
| EP | 1556097 | B1 | 8/2011 |
| EP | 1746941 | B1 | 11/2011 |
| EP | 2395942 | A1 | 12/2011 |
| EP | 2347723 | B1 | 12/2012 |
| EP | 2286739 | B1 | 1/2013 |
| EP | 2604195 | A1 | 6/2013 |
| EP | 1492585 | B1 | 6/2016 |
| EP | 2143387 | B1 | 12/2016 |
| EP | 1647231 | B1 | 11/2017 |
| FR | 2846868 | A1 | 5/2004 |
| FR | 2941858 | A1 | 8/2010 |
| JP | 2000316979 | A | 11/2000 |
| JP | 2005519709 | A | 7/2005 |
| JP | 2005524485 | A | 8/2005 |
| JP | 2007069003 | A | 3/2007 |
| JP | 2007513685 | A | 5/2007 |
| JP | 2010502289 | A | 1/2010 |
| JP | 2012050841 | A | 3/2012 |
| JP | 2012517255 | A | 8/2012 |
| WO | WO-03094785 | A1 | 11/2003 |
| WO | WO-2007045229 | A1 | 4/2007 |
| WO | WO-2008030403 | A1 | 3/2008 |
| WO | WO-2008039223 | A1 | 4/2008 |
| WO | WO-2010002291 | A1 | 1/2010 |
| WO | WO-2010009291 | A1 | 1/2010 |
| WO | WO-2010018571 | A2 | 2/2010 |
| WO | WO-2010092291 | A1 | 8/2010 |
| WO | WO-2011085234 | A1 | 7/2011 |

(56) References Cited

FOREIGN PATENT DOCUMENTS

| | | | |
|---|---|---|---|
| WO | WO-2011120047 | A1 | 9/2011 |
| WO | WO-2013014353 | A1 | 1/2013 |
| WO | WO-2013014355 | A1 | 1/2013 |
| WO | WO-2013026474 | A1 | 2/2013 |
| WO | WO-2014193949 | A2 | 12/2014 |
| WO | WO-2017048989 | A1 | 3/2017 |
| WO | WO-2017191500 | A1 | 11/2017 |
| WO | WO-2017201504 | A1 | 11/2017 |
| WO | WO-2018089773 | A1 | 5/2018 |
| WO | WO-2019077218 | A1 | 4/2019 |
| WO | WO-2020152640 | A1 | 7/2020 |
| WO | WO-2024170414 | A1 | 8/2024 |
| WO | WO-2024194771 | A2 | 9/2024 |

OTHER PUBLICATIONS

Extended European Search Report for European Application No. 22170158.4, mailed Oct. 11, 2022, 8 pages.

Heiss, et al., Treatment of anastomotic leak in colorectal surgery by endoluminal vacuum therapy with the VACStent avoiding a stoma—a pilot study, Langenbeck's Archives of Surgery, 409:234, pp. 1-12 (Jul. 2024).

International Search Report and Written Opinion dated Oct. 2, 2024 in Int'l PCT Patent Appl. Serial No. PCT/IB2024/052550 (061001).

International Search Report and Written Opinion dated Aug. 19, 2022 in Int'l PCT Patent Application Serial No. PCT/US2022/026558, 10 pages (051001).

International Search Report and Written Opinion dated Mar. 20, 2019 in Int'l PCT Appl. Serial No. PCT/FR2018/052388, 06 pages (031001).

International Search Report and Written Opinion dated May 7, 2010 in Int'l PCT Patent Application Serial No. PCT/FR2010/050210, 6 pages (011001).

International Search Report and Written Opinion dated Sep. 4, 2012 in Int'l PCT Patent Appl. Serial No. PCT/FR2012/051576 (021001), 7 pages.

International Search Report and Written Opinion from corresponding PCT Application No. PCT/FR2020/050889, Sep. 10, 2020, 6 pages (041001).

Lange, et al., Clinical implantation of 92 VACStents in the upper gastrointestinal track of 50 patients-applicability and safety analysis of an innovative endoscopic concept, Front. Surg. 10:1182094, doi:10.3389/fsurg.2023.1182094 (May 2023).

Lange, et al., VACStent: Combining the benefits of endoscopic vacuum therapy and covered stents for upper gastrointestinal tract leakage, Endosc. Int. Open, 09:E971-E976 (May 2021).

Moon CM., et al., "Comparison of a Newly Designed Double-Layered Combination Covered Stent and D-Weave Uncovered Stent for Decompression of Obstructive Colorectal Cancer: A Prospective Multicenter Study", Dis Colon Rectum, 2010, vol. 53, pp. 1190-1196.

Mukai, et al., The economic burdens of anastomotic leakage for patients undergoing colorectal surgery in Japan, Asian Journal of Surgery, 46:4323-4329 (2023).

Shim CS., et al., "Through-the-Scope Double Colonic Stenting in the Management of Inoperable Proximal Malignant Colonic Obstruction: a Pilot Study", Endospcopy, 36(05):426-431 (May 2004).

Shomura Y., et al., "Composite Material Stent Comprising Metallic Wire and Polylactic Acid Fibers, and Its Mechanical Strength and Retrievability", Acta Radiol., May 2009, vol. 50, No. 4, pp. 355-359.

SURGICAL DEVICE FOR CONTROLLED ANCHORING IN THE INTESTINE

CROSS-REFERENCE TO RELATED APPLICATIONS

This is a continuation application of U.S. application Ser. No. 19/330,687, filed Sep. 16, 2025, now U.S. Pat. No. 12,558,095, which is a continuation application of U.S. application Ser. No. 19/210,993, filed May 16, 2025, now U.S. Pat. No. 12,433,592, which is a continuation application of U.S. application Ser. No. 18/940,115, filed Nov. 4, 2024, now U.S. Pat. No. 12,324,584, which is a continuation application of U.S. application Ser. No. 18/770,634, filed Jul. 11, 2024, now U.S. Pat. No. 12,137,911, which is a continuation application of U.S. application Ser. No. 18/333,101, filed Jun. 12, 2023, now U.S. Pat. No. 12,042,148, which is a continuation application of U.S. application Ser. No. 18/312,335, filed May 4, 2023, now U.S. Pat. No. 12,048,433, which is a continuation application of U.S. application Ser. No. 17/071,034, filed Oct. 15, 2020, now U.S. Pat. No. 11,857,191, which is a divisional application of U.S. application Ser. No. 15/959,553, filed Apr. 23, 2018, now U.S. Pat. No. 10,835,248, which is a divisional application of U.S. application Ser. No. 14/234,834, filed Jan. 24, 2014, now U.S. Pat. No. 9,980,727, which is a 371 of International Application No. PCT/FR2012/051576, filed Jul. 5, 2012, which claims priority to French Patent Application No. 1156771, filed Jul. 25, 2011, the entire contents of each of which are incorporated by reference herein. This application is also related to U.S. application Ser. No. 15/097,491, filed Apr. 13, 2016, now U.S. Pat. No. 10,456,138, which is a divisional application of U.S. application Ser. No. 13/147,199, filed Aug. 11, 2011, now U.S. Pat. No. 9,339,272, which is a 371 of International Application No. PCT/FR2010/050210, filed Feb. 9, 2010, which claims priority to French Patent Application No. 0950819, filed Feb. 10, 2009, the entire contents of each of which are incorporated by reference herein.

FIELD OF THE INVENTION

The present invention relates to a surgical device for anchoring to the mucous membrane of the inner wall of the intestine, the device comprising an anchor element having at least one first semi-rigid hollow longitudinal element defining a wall forming a surface of revolution about a longitudinal axis with a substantially cylindrical multiply-perforated main portion of substantially circular section referred to as the "first" wall, said anchor element being made of a material giving it radial elasticity properties such that it can be compressed radially into a retracted position and can adopt a said maximally radially expanded position after the radial compression has been released, whereby said first multiply-perforated wall presents a diameter that can be varied in controlled manner.

More particularly, the present invention relates to an anchor device presenting anchoring that can be modified in controlled manner.

BACKGROUND OF THE INVENTION

Elements for anchoring in the intestine are known, in particular devices known as "enteral prostheses" or "digestive stents", which devices present a said first wall formed still more particularly as a mesh of spiral-wound wires, preferably made of nitinol, presenting properties of controlled diameter variation depending on temperature as described below, with an outer diameter that can be varied in controlled manner between:

- a minimum first outer diameter in said radially retracted position of said first wall, preferably of at most 10 millimeters (mm); and
- a maximum first outer diameter in said maximally radially expanded position of said first wall, preferably lying in the range 18 mm to 45 mm.

Still more particularly, the present invention relates to a surgical device suitable for providing temporary protection for an anastomosis in the esophagus, the stomach, the jejunum, the colon, the rectum, or the anal canal.

In WO 2010/092291, and also in other documents such as WO 03/094785 and US 2008/0208357, said anchor element is coupled to an outer flexible sheath that extends in the same longitudinal direction as said stent, on the outside of said stent.

Those devices may be implanted 1) in the small intestine as described in WO 03/094785; 2) in the esophagus as described in US 2008/0208357 to combat obesity; and 3) in the colon, as described in WO 2010/092291 for protecting an anastomosis.

In other applications, in particular to avoid proliferation of cancer, a said stent is used without a said sheath solely for the purposes of providing permanent protection of the zone that is covered by said stent.

In any event, said anchor element must remain anchored in temporary or permanent manner against the wall of the intestine with said sheath extending downstream from said stent. In all of the applications mentioned above, it can happen that said temporary or permanent anchor elements separate from the wall of the intestine and migrate too soon.

In particular in the application of providing temporary protection for an anastomosis as described in WO 2010/092291, provision is made for the temporary anchorage to begin migrating after the end of the post-operative ileus period, which is estimated on average to be three days to five days. As a result, and because said outer sheath presents a length covering the distance between the anastomosis and the anchor site that is at least 50 centimeters (cm) upstream, and that is preferably at least 1 meter (m) upstream, said anchor is thus anchored far enough upstream from the anastomosis to ensure that when the digestive process restarts, the time it takes to migrate from said anchor position to said anastomosis is at least three days, and preferably at least six days.

Thus, insofar as the stage of post-operative intestinal paralysis, known as "ileus", lasts for three to five days, it is possible to protect the anastomosis for that same period plus the time taken, after said anchor element has been released, for it to migrate from its anchor site upstream from the anastomosis to the site of the anastomosis, it being understood that this migration time depends on the distance to be traveled between the anchor site and the anastomosis. In practice, a distance of 50 cm to 1 m gives rise to a migration time of three days to six days, such that, in all, the anastomosis is protected for a duration of at least six days and possibly up to 11 days after making the anastomosis.

Nevertheless, it can happen that the post-operative ileus period is exceptionally short or on the contrary exceptionally long, with periods lying in the range 24 hours to four weeks, such that either the device migrates through the anastomosis before it has had time to heal, or on the contrary the device remains anchored in the intestine for too long.

In order to comply with an appropriate period for remaining within the intestine, it is therefore necessary to take account of the movements specific to the intestine of the operated patient. The greater the activity of the intestine, the faster the migration of the device, it also being understood that it is highly recommended to encourage post-operative intestinal activity in order to improve rapid rehabilitation of the patient.

For curative treatment of anastomotic fistulas after bypass surgery for morbid obesity, US patent No. 2008/0208357 describes a device for protecting the gastro-jejunal anastomosis. According to that patent, a protective sheath is secured to the downstream end of a stent. The stent is positioned in the bottom end of the esophagus where it is to remain in place as a result solely of its own characteristics. The protective sheath passes through the anastomosis and lies in the jejunum. The major drawback of that device consists in the risk of the stent migrating at an unwanted moment, and thus the risk of the entire device migrating into the intestine with at best the need to extract the device by endoscopic maneuvers, and at worse the risk of the intestine becoming occluded or perforated and making further surgery necessary. The risk of esophagus stents migrating remains significant, being about 20% for all stents.

Furthermore, the device described in the prior art for temporary anchorage and for protecting an anastomosis cannot prevent anastomotic fistulas arising, which fistulas take considerably longer to heal than the time the device remains in the intestine, in other words the temporary protection device runs the risk of being eliminated long before healing of a fistula, if there is one. Under such circumstances, the practitioner needs to make a protective stomy, which greatly decreases the therapeutic advantage of the device. From the above, it can be seen that the behavior of a device for providing an anastomosis with temporary protection, or more generally of a device for providing anchoring in the intestine, depends on factors that vary sufficiently between individuals to give it a random character, with the practitioner having no means for modifying the behavior of said anchor element once it has been implanted.

The time the device spends in the intestine depends on many factors such as the characteristics of the stent (radial opening force, resistance to compression, adaptability to deformations of the intestine, shape of the mesh, covering of its surface, etc.), the passive physical properties of the walls of the intestine (viscoelasticity), its dynamic properties (contractility), and also on the consistency of the stools. One of the factors that governs the behavior of the device is the force of friction that exists between the walls of the stent and the intestine. The greater the friction force, the slower the movement of the stent. Unfortunately, the coefficient of friction of the inner walls of the intestine is very low because of the presence of water, thus having the consequence of making it easier for the stent to slide.

This may be compensated in several ways. One consists in increasing the coefficient of friction of the outer walls of the stent by means of a covering film having adhesive properties. It has been shown that a textured surface, in particular when covered with micro-fibrils can present properties of greater adhesion (S. Buhl et al., Humidity influence on the adhesion of biomimetic fibrillar surfaces, International Journal of Materials Research, 2009; 100, No. 8: pp. 1119-1126). Nevertheless, that does not make it possible to exert direct control at will in variable amounts on the device in order to modify its behavior. Another method consists in increasing the diameter of the stent. However, apart from the risk of causing traumatic lesions in the walls of the intestine, that method likewise provides no direct control over the behavior of the stent. Finally, it is possible to use semi-resorbable hybrid stents in which the radial force decreases progressively as they are resorbed (Y. Shomura, Composite material stent comprising metallic wire and polylactic acid fibers, and its mechanical strength and retrievability, Acta Radiol. 2009 May; 50 (4): 355-9). However, once more, the resorption process is not governed by any external action on the intestine, so it does not make it possible to exercise any direct control at will and in varying amounts on the device in order to modify its anchoring properties.

In other indications, digestive stents are used for remedying digestive stenoses. These may be stenoses of the esophagus, in particular those complicated by tracheal-esophageal fistula, gastric and duodenal stenoses, colonic and rectal stenoses. Some such stenoses can be treated by bare stents that serve to reduce the risk of migration at the expense of becoming incrusted in the wall of the intestine. Others are treated by stents covered in a film that serves to reduce the risk of becoming incrusted at the expense of increasing the risk of migrating.

It is thus still sought to provide a device that makes it possible to avoid the stent becoming incrusted in the walls of the intestine, while making it possible to control the risk of untimely migration.

SUMMARY OF THE INVENTION

The object of the present invention is to provide a device that makes it possible to control and to modify at will the behavior of the anchor element in the intestine.

More particularly, the object of the present invention is to provide a novel type of surgical device that makes it possible at will to modify the duration of the period it remains static, i.e. the time that elapses between the device being put into place in the intestine and beginning to migrate, and/or the time the device remains dynamically in the intestine, i.e. the time that elapses between the beginning of the migration of the device and its elimination from the intestine.

Still more particularly, the object of the present invention is to provide a device for which migration can be slowed down and/or interrupted in the event of anastomotic fistulas appearing so as to allow said fistula to heal before said device migrates to the level of said fistula.

To do this, the present invention consists essentially in taking advantage of the viscoelasticity of the intestine in order to cause its inner wall known as its "mucous membrane" to be attracted towards the outer wall of the stent. The intestine or mucous membrane is flexible and elastic, whereas the walls of the stent are relatively rigid. The intestine wall can be attracted (by suction) so as to be placed adjacent to the outer walls of the stent under the effect of negative pressure in the interface between the stent and the mucous membrane. Under such circumstances, the force of friction between the intestine and the stent increases rapidly and significantly by a kind of suction cup effect. Conversely, in the present invention, this suction effect can be modified or eliminated by injecting air or a liquid solution between the stent and the mucous membrane of the intestine. Consequently, the mobility of the stent becomes closely tied to the suction effect, and modulating that effect then makes it possible to act on the behavior of the stent in the intestine.

More precisely, the present invention provides a surgical anchor device suitable for being anchored in the mucous membrane of the inner wall of the intestine, the device comprising a temporary anchor element of anchoring that can be modified in controlled manner, comprising at least a first semi-rigid hollow longitudinal element defining a wall in the form of a surface of revolution about a longitudinal axis having a substantially cylindrical multiply-perforated main portion of substantially circular section referred to as a "first" wall, said first hollow longitudinal element being made of a material that gives it properties of radial elasticity such that it can be compressed radially into a retracted position and can adopt a said position referred to as a maximally radially expanded position after the radial compression has been released, whereby said first multiply-perforated wall presents a first outer diameter that can be varied in controlled manner between:

- a minimum first outer diameter in said radially retracted position of said first wall of at most 20 mm, preferably of at most 10 mm; and
- a maximum first outer diameter in said maximally radially expanded position of said first wall, preferably lying in the range 18 mm to 45 mm;
- the device being characterized in that at least a portion and preferably all of the length of the cylindrical inner surface of said first wall is lined with an independent leakproof layer forming an inner sheath, only the longitudinal ends of said inner sheath being fastened in leaktight manner to said anchor element with the help of first leaktight fastener means, preferably respective annular elastomer adhesive gaskets, at each of said longitudinal ends of said inner sheath, so as to define a chamber referred to as a suction chamber between said inner sheath and said first wall, said temporary anchor element being coupled to a flexible or semi-rigid tube referred to as an injection-suction tube extending outside said anchor element, an open end of said injection-suction tube opening out into said suction chamber.

More particularly, said injection-suction tube is connected, preferably reversibly, at its free longitudinal end to a connection endpiece, itself connected reversibly or suitable for being connected reversibly with a device such as a syringe for injecting or sucking air or liquid, said connection endpiece including a shutter device, preferably an anti-reflux valve, and a vacuum indicator device suitable for indicating the degree of vacuum in said suction chamber at the other end of said injection-suction tube, said indicator device preferably being a balloon.

It can be understood that said device for indicating the extent of the vacuum indicates the extent of the vacuum in said suction chamber while said surgical device of the invention is in place against the inner wall of the patient's intestine, thus making it possible to monitor and control or modify the anchor force of the device of the invention against the wall of the intestine.

It can be understood that said injection-suction tube is a semi-rigid tube made in particular of polyethylene (PE) or of polypropylene (PP), and that it presents a length suitable for remaining in shape and extending inside the intestine from an anal or nasal orifice of the patient to said anchor element, with the length of said injection-suction tube preferably being at least 20 cm, and more particularly lying in the range 50 cm to 150 cm, and with the free end of said injection-suction tube outside the patient being connected to a device for sucking or injecting gaseous fluid or liquid, in particular air or a cold liquid as explained below.

It can be understood that said chamber defines a leaktight chamber between the leakproof film of the inner sheath and the wall of the intestine when said anchor element is in its maximally expanded position and is held stationary by being anchored against the inner surface of the wall of the intestine. In the event of said anchor element being released and/or in the event of said anchor element migrating too quickly inside the intestine, said chamber loses its leaktightness. However, it is then possible to suck air through said tube from its free end outside the patient in order to attract the wall of the intestine by suction against the outer surface of said first wall of part or even all of the outer surface of said first wall defining said chamber in order to slow down migration of the anchor element and possibly even to hold it in place and reestablish a vacuum in said chamber, and thus reestablish leaktightness of said chamber.

Conversely, in order to cause the anchor element to migrate and/or in order to accelerate its migration, it is possible to inject air or a liquid solution into the suction chamber by using said injection-suction tube.

When using stents made of nitinol, the shape memory of that alloy makes it possible to change the shape and the stiffness of the alloy as a function of ambient temperature. More particularly, at ambient temperatures situated below 15° C., nitinol becomes flexible and malleable. Thus, injecting a cold liquid at a temperature in the range 0° C. to 15° C. into the suction chamber makes it possible to make the stent malleable and thus facilitates moving it as it passes through the anastomosis or a zone of narrowing, for example.

The term "first leakproof fastener means" is thus used to mean that said means extend annularly all around the perimeter of said inner sheath in cross-section at its longitudinal ends, and constitute leaktight lateral walls for defining said chamber, where applicable around said injection-suction tube passing through said first leaktight fastener means, as explained below.

Concerning said anchor element, and in known manner, the following terms are used as follows:

- "semi-rigid" means that said first wall of said anchor element remains in each of its retracted or expanded positions in a given shape defining a said surface of revolution; and
- "outer diameter that can be varied in controlled manner" means that the diameter of said first wall may be varied in determined manner as a function of the conditions in which the device is used, regardless of whether this involves parameters such as temperature, and/or independent mechanical means co-operating with said anchor element such as an instrument for putting it into place, and in particular an "introducer" as explained below. Preferably, said inner sheath is constituted by a leakproof film (i.e. having no perforations) that forms a flexible tubular wall.

This embodiment makes the device easy to fabricate and also provides greater sensitivity and greater uniformity in the modulation of the suction effect on injecting/sucking air or liquid through said injection-suction tube.

Nevertheless, in another embodiment, said inner sheath may be formed by a second semi-rigid hollow longitudinal element defining a second wall presenting properties similar to said first hollow longitudinal element as explained below. Under such circumstances, said injection-suction tube is interposed between said multiply-perforated first wall and a second wall that is leakproof or multiply-perforated but covered in a leakproof film on its outer surface.

In a preferred embodiment, the end of said injection-suction tube opening out into said chamber is constituted by a multiply-perforated tube portion extending inside said chamber, preferably substantially over the entire length of said chamber, also preferably in the form of a Z-shaped line running substantially helically along said suction chamber and stuck to the inner surface of said anchor element.

It can be understood that, at its end situated in the suction chamber, the injection-suction tube is provided with multiple lateral perforations.

This embodiment is preferred since it makes it possible to manage the pressure in said suction chamber in more uniform manner over its entire length. The Z- (or zigzag) shape of the injection-suction tube enables it to be folded up in more compact manner when shrinking the diameter of said first wall or of said second wall of the anchor element.

According to another characteristic that is particularly advantageous for ease of fabricating the device, the end of said injection-suction tube opening out into said suction chamber passes in leaktight manner through one of said first fastener means, preferably a said annular adhesive gasket, at one of the longitudinal ends of said inner sheath.

The term "passes in leaktight manner through" is used to mean that the connection between the outer surface of the tube and the orifice via which it passes through said first fastener means or said inner sheath, is leaktight.

For numerous applications in particular to protecting anastomoses, the device advantageously further includes an outer sheath having a tubular wall constituted by a flexible film fastened to said anchor element at one of the longitudinal ends of said anchor element. More preferably, for reasons of ease of fabrication, said outer sheath constitutes an extension of said inner sheath extending outside said anchor element, in particular in the longitudinal direction thereof, and still more particularly, downstream therefrom.

The term "outer sheath" is used herein to mean a sheath that extends outside said anchor element. However, in another embodiment, the inner sheath and the outer sheath may be made of two different elastomer materials.

Said inner and outer sheaths may be two portions of a single sheath.

When the device of the invention is implanted in the esophagus, as described in US 2008/0208357, the injection-suction tube extends outside the stent, upstream therefrom, while said outer sheath always extends downstream from the stent. The injection-suction tube runs along the lumen of the esophagus towards the oropharynx, passes into one of the nasal cavities, and leaves through the corresponding nasal orifice. The path of the injection-suction tube is the path followed by the naso-gastric suction tube always put into place through the anastomosis in order to suck up digestive secretions and avoid air accumulating in the stomach during the post-operative stage. The device of the present invention enables the device to be retained in the esophagus by the above-described suction effect.

The device of the present invention may also be used after resection of the middle and bottom thirds of the esophagus, and after total or partial resection of the stomach for various pathologies, and in particular neoplastic pathologies. Eso-gastric anastomoses or intra-thoracic eso-colonic anastomoses involve a considerable risk of fistulas having severe septic consequences in the interpleural space, representing the main cause of death in these post-operative patients.

In other applications, in particular for devices for providing temporary protection of anastomoses in the colon, where the injection-suction tube is inserted via the anal orifice and not via the nasal cavity or the mouth cavity, said injection-suction tube and said outer sheath extend outside said anchor element from the same end of said anchor element and preferably said injection-suction tube and said outer sheath are secured to each other.

The securing of the injection-suction tube against the wall of said outer sheath, in particular by adhesive, avoids it becoming twisted against itself and/or turning one over the other giving rise to knots or other obstacles to proper extension of said tube and/or of said outer sheath outside said anchor element.

Also preferably, said injection-suction tube is situated outside said outer sheath, i.e. on the outside in the radial direction in cross-section, in this example.

This embodiment is preferred since it makes it possible to handle the tube more easily than if it were situated inside said outer sheath, not to mention the hindrance that would arise from interference with the organic material passing along the inside of said outer sheath once the digestive process has restarted.

In a variant, said injection-suction tube is incorporated within the tubular wall of said outer sheath.

In an advantageous embodiment, the device of the invention is characterized in that said anchor element includes a second semi-rigid hollow longitudinal element defining a wall in the form of a surface of revolution around said longitudinal axis (XX) having a substantially cylindrical multiply-perforated main portion of substantially circular section referred to as a "second" wall, said second wall being arranged coaxially inside said first wall, the longitudinal ends of said second wall being fastened in leaktight manner to the ends of said first wall with the help of first or second leaktight fastener means, preferably respective annular elastomer adhesive gaskets at each of said longitudinal ends of said second wall, said second hollow longitudinal element being made of a material giving it properties of radial elasticity such that it can be compressed radially into a said retracted position and can adopt a said maximally radial expanded position whereby said second outer diameter of said second wall can vary in controlled manner between:

- a minimum second outer diameter (D2') in the radially retracted position of said second wall that is less than said minimum first outer diameter; and
- a maximum second outer diameter (D2) in the maximally radially expanded position of said second wall that is less than said maximum first outer diameter.

More particularly, said second multiply-perforated wall is interposed between said inner sheath and said first wall, the end of said injection-suction tube preferably opening out into said suction chamber between said inner sheath and said second wall.

In an embodiment, the spacing between said maximum second outer diameter and said maximum first outer diameter is at least 0.2 mm, preferably lies in the range 0.2 mm to 10 mm, and more preferably in the range 1 mm to 5 mm.

In another embodiment, said second wall is covered in said inner sheath, with said, preferably multiply-perforated, open end of said injection-suction tube being interposed between said multiply-perforated first wall and the multiply-perforated second wall covered in said sheath, said sheath possibly covering the outer surface or preferably the inner surface of said second wall.

In a particular embodiment, said first wall presents:

a) a length of at least 30 mm, preferably lying in the range 40 mm to 150 mm, and an outer diameter that may be varied in controlled manner between a minimum outer diameter in the radially retracted position of said first wall of no more than 10 mm, and a maximum outer diameter in the maximally radially expanded position of said first wall lying in the range 18 mm to 45 mm, preferably in the range 20 mm to 35 mm; and b) preferably, at least one of its longitudinal ends, more preferably its upstream end, having a flared extension referred to as a "collar", defining a wall in the form of a surface of revolution about said longitudinal axis with a circular section of increasing diameter, having a length preferably lying in the range 5 mm to 30 mm, more preferably in the range 15 mm to 20 mm, and a maximum diameter equal to at least 105% of said maximum first diameter and preferably lying in the range 105% to 150%, in particular with DO lying in the range 20 mm to 40 mm.

This embodiment is particularly advantageous, in particular when the outer face of the first wall is covered in a multiply-perforated elastomer layer, since the function of the collar is to slow down the migration of the device inside the intestine, even after it has ceased to be anchored against the inner wall of the intestine via its main longitudinal portion or outer surface of its first wall, in particular once the digestive process has restarted.

In a preferred embodiment, said second hollow longitudinal element includes a second wall fitted against the inner surface of said first wall, said first and second walls preferably being of the same length.

This embodiment is preferred since said anchor element as constituted in this way by two stents exerts increased radial force so that it remains anchored against the wall of the intestine during a period that is sufficiently long after post-operative restarting of the digestive process. This appears to result from the fact that the two stents secured together serve to stiffen said anchor element overall. Furthermore, the thickness of said first and second walls as juxtaposed in this way creates sufficient spacing between said inner sheath and the wall of the intestine to avoid the perforations of the injection-suction tube in said suction chamber becoming clogged by the inner sheath being stuck against said wall of the intestine, as mentioned above.

It can be understood that this embodiment presents the advantage of permanently maintaining an annular separation space between said inner sheath and said wall of the intestine, resulting from the spacing between the first and second walls, thus making it easier to control the extent of the vacuum in said suction chamber. Since said inner sheath is a leakproof flexible film, it can be difficult to separate it uniformly from the wall of the intestine, should that be necessary as a result of an excessive suction effect.

Also preferably, each said first and second hollow longitudinal element includes at one of the longitudinal ends of each said first and second walls respectively a flared extension referred to as a "collar", defining a surface of revolution about said longitudinal axis (XX) with a circular section of diameter that increases from the end of said first or second wall towards the end of the corresponding said first or second hollow longitudinal element, and of maximum diameter (DO) equal to at least 105% of said maximum first diameter (D1) and preferably lying in the range 105% to 150%, said two hollow longitudinal elements being engaged one inside the other and head to tail so that said anchor element has a said collar at each of its longitudinal ends.

It can be understood that the two stents are engaged one inside the other via their ends that do not have collars.

Such a collar makes it possible to obtain a larger diameter over a shorter length and thus to obtain better adhesion while limiting the risk of perforating the intestine.

Shim et al. have described a technique for treating neoplastic stenoses of the colon using two coaxial stents engaged one within the other (C. S. Shim et al., Double colonic stenting in proximal malignant colonic obstruction, Endoscopy 2004; 36:426-431). That involves two individual stents, put into place in the lumen of the colon, separately and one after the other, each by means of its own introducer.

Moon et al. have also reported experiments with a double stent based on nitinol (C. M. Moon et al., Comparison of a newly-designed double-layered combination covered stent and D-Weave uncovered stent for decompression of obstructive colorectal cancer: a prospective multicenter study, Dis Colon Rectum 2010; 53:1190-1996). The two stents are identical, being fabricated from a two-strand nitinol wire with open mesh without any securing element between the two stents, thereby conferring a large amount of radial and longitudinal deformability thereto and making them easier to introduce into the 3 mm operator canal of the coloscope. A non-perforated film is interposed between the two stents. The outer stent serves to provide good incrustation against the wall of the intestine, while the inner stent is covered in a layer of a non-perforated film that prevents the tumor proliferating inside the inner stent and thus preserves an unobstructed passage inside the inner stent. In contrast, those prior art double stents do not define a suction chamber in accordance with the present invention and/or they do not co-operate with a said injection-suction tube, suitable for controlling the anchor properties and/or the migration of said anchor element from outside. Furthermore, the two stents of the present invention are preferably single-strand stents with securing elements and with practically no longitudinal deformation, as explained below.

In an embodiment, said outer sheath is stuck to the inner face of the downstream collar. In another embodiment, the inner surface of one of the two collars is covered in a biocompatible non-perforated leakproof film.

Still more particularly, said outer sheath at rest presents a length downstream from said anchor element of at least 50 cm, preferably of at least 1 m, with an outer diameter lying in the range 18 mm to 45 mm, and preferably in the range 20 mm to 35 mm.

That device is particularly useful for providing temporary protection of an anastomosis in the colon, the rectum, or the anal canal.

Under such circumstances, and in known manner, the smaller outer diameter D'1 in the radially retracted position of said first wall enables said anchor element to be inserted anally in said radially retracted position and then taken along the colon to a temporary anchor position upstream from the anastomosis in the colon, the rectum, or the anal canal. The maximum outer diameter D1 in the maximally radially expanded position of said wall enables said anchor element to remain anchored temporarily, being held by the radial expansion force against the wall of the intestine in the absence of any matter passing along the intestine, and is suitable for being released and for starting to migrate when the intestine contracts and expands during so-called "peristalsis" once the digestive process has restarted.

It can be understood that said anchor element may then adopt:

- a small outer diameter D'1 of said first wall that is at least less than the diameter of the intestine at rest, and preferably less than 10 mm, so as to be suitable for being introduced anally to upstream of an anastomosis in the intestine; and
- a maximally radially expanded outer diameter D1 of said first wall that is greater than or equal to the diameter of the intestine at rest so as to be capable of being anchored temporarily by pressing against the wall of the intestine as a result of the radial expansion of at least a portion of said anchor element, where D1 is nevertheless smaller than the maximum diameter of the intestine when working in peristalsis so that said anchor element remains fastened against the wall of the intestine in the absence of any matter passing along the intestine, in particular during the post-operative stage of intestinal paralysis known as ileus, but is no longer fastened to the intestine and in practice begins to migrate when the digestive process restarts, the device sliding along the wall of the intestine.

One conventional way of determining D1 is to calibrate the section of one of the ends of the intestine by means of instruments referred to as "bougies" and commonly used by surgeons. Another way of determining D1 is to consider it as being equal to the diameter of the circular stapler inserted for making the mechanical anastomosis, where applicable. Under such circumstances, D1 may more particularly lie in the range 18 mm to 33 mm, corresponding to the outside diameters of the staples that are currently commercially available.

The term "longitudinal end" is used to mean an end in the longitudinal direction of said anchor element or, where appropriate, of said outer sheath.

The term "at rest" when used concerning the length and the diameter of the outer sheath refers to its length and diameter when its elasticity is not involved, respectively in the longitudinal and radial directions.

After the digestive process has restarted, peristalsis of the intestine causes said anchor element to be released and to migrate, however the radial expansion properties of the anchor element enable its outer wall to continue sliding in contact with the inner wall of the intestine and also to obtain sufficient leaktightness to prevent the fecal bolus from passing between the outer wall of the anchor element and the inner wall of the intestine, thereby continuing to protect the anastomosis. It is essential for the fecal bolus to pass inside the outer sheath and to be kept well separated from the walls of the intestine in the vicinity of the anastomosis.

The values given above for the diameter in radial expansion of the anchor element correspond to values that are slightly greater than the diameter of the intestine at rest in some individuals, but less than the 30 mm to 60 mm value of the maximum diameter of the intestine as expanded during the digestive process. In addition, the length of said main portion is such that the contact area between said anchor element and the wall of the colon combined with the radial expansion force are such that said anchor element in the maximally expanded position is suitable for remaining stationary temporarily as a result of its radial expansion force against the wall of the intestine upstream from the anastomosis, so it does not migrate for at least three days and preferably for five days after it has been anchored and in the absence of the digestive process. If the main portion does not have a length of at last 30 mm in contact against the colon, then said anchor element cannot remain anchored for at least three days without having recourse to fastener means, thus requiring means and/or surgery to deactivate those fastener means and allow the element to migrate, or without having recourse to anchor means that present a maximally expanded diameter that is greater and that could injure the colon and above all that could prevent the anchor element being released naturally when the digestive process restarts.

Furthermore, the length of the outer sheath is such that the distance between the anastomosis and the anchor site upstream therefrom may be at least 20 cm, and preferably at least 50 cm, and said anchor element may be anchored in the colon far enough upstream from the anastomosis so that when the digestive process restarts, the time it takes to migrate from said anchor position to said anastomosis is at least three days and preferably at least six days, with said outer sheath protecting the anastomosis and possibly extending beyond the anal orifice when said anchor element is in the anchor position.

Thus, insofar as the stage of post-operative intestinal paralysis known as "ileus" lasts for three days to five days, it is possible to protect the anastomosis for this same period plus the length of time taken, after said anchor element has been released, for it to migrate from its anchor site upstream from the anastomosis to the site of the anastomosis, it being understood that this migration time depends on the distance to be traveled between the anchor site and anastomosis. In practice, a distance of 50 cm to 1 m leads to a migration time of three days to six days, such that the anastomosis is protected in all for a duration of at least six days and up to 11 days after the anastomosis is made.

Advantageously, said inner and outer sheaths (7) are made of biocompatible synthetic material, having a wall thickness of 0.01 mm to 1 mm, preferably being made of silicone or polyurethane type elastomer materials having thickness in the range 0.05 mm to 1 mm, and more preferably presenting properties of radial and longitudinal elasticity, and at least said outer sheath presenting shape memory properties and non-stick properties.

It can be understood that by being made of elastomer, said outer sheath presents properties of being radially and longitudinal stretchable that are similar to those of the wall of the intestine, which properties are those of an elastomer material forming said outer sheath, which presents properties of radial and longitudinal elasticity. These properties of radial and longitudinal elasticity of the outer sheath are similar to those of the wall of the colon and thus allow matter to pass through the intestine properly inside said outer sheath throughout the entire duration of the migration of the anchor element, i.e. a duration of at least six days and up to ten days.

The longitudinal elasticity of the elastomer outer sheath may be greater than that of the intestine without giving rise to any difficulty, indeed that presents the advantage of it being possible to pull on the portion of the outer sheath that has passed through the anus so as to cut off the end of the sheath, which then retracts back inside upstream in the rectum.

Because of its radial elasticity, said longitudinal end of the outer sheath remains fastened to said end of said anchor element regardless of the extent to which it has been expanded radially.

Furthermore, the thickness characteristics of the outer sheath in combination with its elasticity give it a shape memory property. The term "shape memory property" is used herein to mean that the elastomer material constituting said outer sheath naturally returns to its initial shape after it has been deformed in folding. Given the great length of the outer sheath, these shape memory properties are important so that the material naturally returns to its longitudinal shape without creating any blockage to the passage of material through the intestine in the event of the outer sheath becoming folded, as can happen during its migration after the release of the anchor element.

The term "non-stick properties" is used to mean that the elastomer material constituting said outer sheath presents a coefficient of adhesion such that the two opposite surfaces of the inner wall of the outer sheath do not stick to each other in the event of folding, so as to ensure that no resistance is created against passing gas and matter.

Said anchor element may be held in its radially retracted position with an instrument referred to as an "introducer"

and described below, with radial expansion taking place after the anchor element has separated from the introducer.

It can also be understood that:

- said outer sheath presents a diameter at rest that is substantially not less than said small outer diameter D'1 of said hollow anchor element when it is radially retracted, and less than the diameter of the intestine at rest, and preferably said diameter at rest of said outer sheath is substantially equal to the diameter at rest of the wall of the intestine at rest; and
- said outer sheath extends downstream from the end of said anchor element to which it is fastened over a length corresponding to the distance between the anchor position upstream from said anastomosis and a downstream position preferably going as far as the anal orifice.

Said first wall, and where appropriate said second wall, of said anchor element are multiply-perforated, in particular by pores or mini-perforations.

In a particular embodiment, said first and second hollow longitudinal elements for temporary anchoring are stent type enteral prostheses.

Said first tubular wall may be covered over at least its outer face in a multiply-perforated covering made of biocompatible synthetic material, preferably an elastomer of the silicone or polyurethane type. This outer covering is doubly advantageous in that it makes it easier to release said anchor element by sliding along the wall of the intestine when the digestive process restarts, and during anchoring it protects the wall of the intestine against which said longitudinal element has expanded, which might otherwise give rise to incrustation in the tissue of the wall and prevent subsequent release, or possibly even lead to perforation of the wall of the intestine.

Such enteral prostheses of the type known as "stents" have been used with intestinal tumors for about 20 years, namely for palliative treatment of tumoral stenoses (narrowings) of the esophagus, of the duodenum, and of the colon.

Said temporary anchor element is preferably constituted by one or more enteral prostheses formed by an open mesh of spiral-wound metal wires or plastics filaments, in particular based on polyethylene, and possibly covered in a layer of biocompatible synthetic material covering said mesh, said covering preferably being made of a biocompatible elastomer material such as silicone.

In known manner, radial expansion is then the result of the crossing of the metal wires with angle variation making it possible to vary the width of the lozenges or parallelograms of the meshes of said mesh of spiral-wound wires.

Preferably, and in known manner, a stent is used of a design and a shape for the spiral-wound wire mesh that makes it possible to obtain variation in the diameter of said stent with minimum variation in its length, preferably with practically no variation in its length on being compressed radially.

Advantageously, said anchor element is made of a material that gives it said ability to expand by radial elasticity only at a temperature that is not less than ambient temperature (20° C.), and in particular at the temperature of the human body, said anchor element being in said retracted radial position at a temperature lower than said ambient temperature, and preferably lower than 5° C. It can be understood that the material of tubular shape changes diameter automatically as a function of ambient temperature.

Still more particularly, said anchor element is made up of one or more enteral prostheses formed by a mesh of spiral-wound wires, preferably made of nitinol.

Nitinol is a metal alloy presenting radial expansion properties that vary progressively as a function of temperature at a temperature greater than or equal to ambient temperature (25° C.), thus enabling it to conserve its retracted shape at colder temperatures, in particular at 4° C. during storage. Once retracted at low temperature, it thus remains retracted for a length of time that is sufficient to enable it to be moved into the intestine with the help of said introducer. Once it has been released inside the intestine, the prosthesis progressively expands radially under the effect of higher ambient temperature, i.e. the temperature of the human body.

More particularly, the thickness of said first wall of the anchor element lies in the range 0.1 mm to 1 mm, and preferably in the range 0.2 mm to 0.5 mm.

This is more particularly the thickness of the wire forming said first wall when it is constituted by a stent made of a mesh of spiral-wound wires.

In order to satisfy the radial expansion properties of the elastomer sheath, and given the thicknesses involved (0.01 mm to 0.1 mm), it is necessary to use elastomer compositions that present a certain amount of hardness, and also a certain coefficient of adhesion, and a certain amount of shape memory (compression set), with values that are selected to lie within ranges that are specified below.

More particularly, said outer sheath at least and preferably both said inner and outer sheaths is/are made of biocompatible polymer material based on elastomer that is preferably of the silicone type and/or of the polyurethane type, and presenting the following properties:

- hardness on the Shore A scale lying in the range 5 to 95, and preferably in the range 50 to 70;
- compression set lying in the range 10% to 35%, preferably in the range 17% to 23%; and
- coefficient of friction lying in the range 0.30 to 0.90, preferably in the range 0.35 to 0.45.

The term "hardness" is used to mean the elastic deformation energy of an elastomer expressed on the Shore A scale, e.g. in accordance with the DIN 53505 standard.

The term "compression set" is used to mean the residual deformation that remains after a sample of elastomer has been relieved of a load that has been applied for a determined length of time in compliance with the test of the DIN 53517 ISO 815B standard, e.g. the property of shape memory on folding, the material returning to an unfolded shape as soon as the compression that gave rise to the folding is released.

The term "coefficient of friction" may be measured using the ASTM D1894 standard, for example.

The above-mentioned values for the coefficient of friction ensure that there is no adhesion between the two opposite faces of the inner wall of the sheath, one to the other, so as to avoid creating any resistance to the passage of gas or of matter through the sheath, and also to ensure that in the event of the sheath folding it does not become blocked by closing on itself.

Still more particularly, said sheath is made of a biocompatible polymer material based on silicone comprising at least the following compounds:

- an elastomer having the liquid silicon rubber (LSR) grade or quality in a proportion by weight lying in the range 75% to 95%;
- an elastomer having the room temperature vulcanizing (RTV) grade or quality in a proportion by weight lying in the range 2.5% to 12.5%; and
- an elastomer having the gel grade or quality in a proportion by weight lying in the range 2.5% to 12.5%.

This combination of elastomers of different grades (LRS+RTV+gel) is advantageous because:

an elastomer of the LSR grade or quality provides resistance to tearing;

an elastomer of the RTV grade or quality provides properties of radial and longitudinal elasticity; and an elastomer of the gel grade or quality provides a small coefficient of adhesion (non-stick).

In an embodiment, said anchor element is an enteral prosthesis of the stent type covered on at least its outer face in a multiply-perforated covering of an elastomer synthetic material of the silicone or polyurethane type, said elastomer covering, where applicable, being more flexible than the elastomer material constituting said sheath, the connection between said sheath and said anchor element being by said anchor being overlapped by said sheath over a fraction only of the length of said anchor element.

Stent type enteral prostheses of this type that are covered in elastomer, in particular in a silicone-based elastomer, are well known and commercially available.

Thus, the elastomer covering the stent presents greater radial and longitudinal deformability than does the elastomer of the sheath, i.e. the elastomer of the covering of the stent is constituted, where appropriate, by a mixture of different types of silicone that presents a content by weight of the RTV grade that is greater than the content of the elastomer of the sheath, while still remaining within the above-mentioned range of 2.5% to 12.5%.

As explained below, this embodiment makes it possible, by exerting traction on the sheath, to reduce the diameter of the stent and to lengthen it axially, thereby enabling it to be separated from the intestine in order to facilitate its migration through the anastomosis when said anchor element is released.

The coefficient of friction of the outer surface of the anchor element may be increased by means of a covering film having adhesive properties, presenting an outer surface that is textured, in particular being covered in micro-fibrils, as described above.

Also advantageously, a said anchor element of the stent type is used that has an elongate or filiform extension at its end, referred to in conventional manner as a “lasso”, which extension enables traction to be applied to the end of said stent type anchor element in a manner that is known to the person skilled in the art, possibly using a tool such as a coloscope, for the purpose of facilitating release and/or migration through the zone of the anastomosis when that is desired, in order to avoid blockage of the element.

Advantageously, said polymer material of said sheath includes radio-opaque filaments, in particular made of barium sulfate, that are arranged in the longitudinal direction of the tube.

These filaments make it possible to follow the migration of the tube of the sheath and to monitor its initial position and then its progressive migration while it is being eliminated. Furthermore, the longitudinal positioning of such filaments also gives the sheath resistance to lengthening, thereby reducing its longitudinal elasticity, which can be excessive relative to that of the intestine, as explained above.

Advantageously, the sheath is graduated in the increasing direction starting from its upstream end.

More particularly, the introducer may, in known manner, be constituted by a semi-rigid guide tube of the catheter type that is provided at one of its ends with a handle and that has an inside diameter and a length that make it possible to keep said anchor element housed therein in its retracted shape together with said sheath, which is preferably deployed longitudinally.

For introduction by the anal passage, said device preferably also comprises an instrument known as an introducer and comprising:

a tubular outer shell suitable for containing and holding said anchor element compressed in said retracted position and said injection-suction tube inside the distal end of said outer shell, and long enough also to contain said sheath and said injection-suction tube, said outer shell preferably having a length of at least 70 cm, and more preferably of at least 100 cm;

means for bringing the distal end of said introducer from the anal orifice to said anchor site in the intestine upstream from the anastomosis; and preferably, means for separating said anchor element from the outer shell, more preferably consisting in a pusher tube carrying an abutment at its distal end, where appropriate in contact with the longitudinal end of said anchor element, said sheath downstream from the anchor element surrounding said pusher tube inside said outer shell.

The withdrawal of the outer shell, and then of the pusher tube makes it possible to deploy the sheath completely downstream from the anchor element without the surgeon needing to perform any additional maneuver to deploy the sheath.

Also preferably, the device of the invention has a protective tube having a portion of curved shape matching the curvature of the concave side of the sacrum, rigidity greater than that of the outer shell of the introducer, an outside diameter and a length suitable for enabling said protective tube to be inserted via the anal orifice and to extend from the anal orifice to upstream of said anastomosis, and an inner diameter and a said curvature matching the curvature of the concave side of the sacrum, such that said protective tube is suitable for containing said introducer and for allowing it to be moved from the anal orifice to said anastomosis, preferably a protective tube having an outer diameter lying in the range 20 mm to 40 mm and a length lying in the range 10 cm to 25 cm.

The present invention also makes it possible to use a surgical device of the invention to perform a surgical treatment method in which the following successive steps are performed:

1) inserting a said surgical device by an anal or nasal passage and taking it to an anchor site in the intestine, said anchor element being held in said radially retracted position D'1 and moved with the help of an instrument known as an introducer, and said injection-suction tube being of a length not less than the distance between the anchor site and the anal or nasal orifice;

2) separating the introducer from said anchor element once it has been taken to said anchor site so as to enable said anchor element to adopt a said anchor position against the wall of the intestine in said maximally radially expanded position;

3) where appropriate, sucking air from the free end of said injection-suction tube outside the patient in order to prevent said anchor element from migrating and/or in order to slow down migration of said anchor element; and 4) where appropriate, injecting air and/or a liquid into the free end of said injection-suction tube, in particular injecting a cold liquid, in order to facilitate and/or accelerate migration of said anchor element in the intestine.

In above step 1), said elastomer outer sheath is of a length not less than the distance between the anchor site and the anal orifice or of a length of at least 10 cm downstream from the anchor site in the esophagus, said length preferably lying in the range 20 cm to 50 cm.

The method is useful in particular for providing temporary protection of an anastomosis in the large intestine or colon, the rectum or anal canal, in order to prevent or reduce any risk of anastomotic fistula. Under such circumstances, and preferably, the distance between said anchor position upstream from said anastomosis and said anastomosis is not less than the distance traveled in at least three days and preferably in at least five days by said anchor element during its migration once it has been released from said wall of the intestine as a result of the digestive process restarting.

More particularly, the distance between the anastomosis and said anchor site is at least 20 cm, and preferably at least 50 cm.

Said introducer is preferably introduced into the anal orifice by being pushed along the inside of a semi-rigid protective tube having a curved portion matching the curvature of the concave side of the sacrum, the rigidity of the tube being greater than that of the outer shell of the introducer, said protective tube having an outer diameter and a length making it suitable for being introduced via the anal orifice so as to extend from the anal orifice to a point immediately upstream from said anastomosis, and having an inner diameter and a said curvature matching the curvature of the concave side of the sacrum, such that said protective tube is suitable for containing said introducer and for enabling it to be taken from the anal orifice to said anastomosis, which tube extends from the anal orifice to said anastomosis, the protective tube preferably having an outer diameter lying in the range 20 mm to 40 mm and a length lying in the range 10 cm to 25 cm.

Also preferably, after said migrating anchor element has been released from said wall of the intestine as a result of the digestive process restarting, it is recovered in a semi-rigid protective tube having a curved portion matching the curvature of the concave side of the sacrum, the rigidity of the tube being greater than that of the outer shell of the introducer, said protective tube having an outer diameter and a length making it suitable for being introduced via the anal orifice so as to extend from the anal orifice to a point immediately upstream from said anastomosis, and having an inner diameter and a said curvature matching the curvature of the concave side of the sacrum, such that said protective tube is suitable for containing said introducer and for enabling it to be taken from the anal orifice to said anastomosis, which tube extends from the anal orifice to said anastomosis, the protective tube preferably having an outer diameter lying in the range 20 mm to 40 mm and a length lying in the range 10 cm to 25 cm.

The above-mentioned introducer devices and protective tubes are described in greater detail in WO 2010/092291.

In a preferred embodiment, in particular when said anchor element includes a collar, preferably a collar at each end, a yarn referred to as a "lasso" is attached to the margin of said collar, with preferably at least one of the two yarns being of a length not less than the length of said injection-suction tube, and where appropriate of said outer sheath.

When protecting an anastomosis with introduction via the anal orifice, the lasso attached to the upstream collar passes through the lumen of the anchor element and, where appropriate, of the outer sheath downstream in order to extend to the outside downstream through the anal orifice, said outer sheath being attached to the downstream end of the main portion of said anchor element upstream from the downstream collar, preferably in continuity with said inner sheath.

When protecting the esophagus with introduction via the nasal or mouth orifice, the lasso attached to the upstream collar passes outside said injection-suction tube upstream from the anchor element and extends to the outside through the nasal or mouth orifice, while the lasso attached to the downstream collar passes:

- either outside the anchor element between the main portion of said anchor element and the mucous membrane, and then outside said upstream injection-suction tube in order to pass to the outside upstream through the nasal or mouth orifice, in the presence of a downstream outer sheath;
- or else through the lumen of the anchor element and outside the upstream injection-suction tube in order to pass to the outside upstream through the nasal or mouth orifice, in the absence of a downstream outer sheath.

The advantage of such a lasso is to make it possible to reduce the maximum diameter of the collar and thus the adhesion of the collar on the mucous membrane by pulling on the end of the lasso, since the collars are anchored more intimately in the mucous membrane than is the main portion of the anchor element.

BRIEF DESCRIPTION OF THE DRAWINGS

Other characteristics and advantages of the present invention appear in the light of the following detailed description made with reference to FIGS. 1 to 6, in which.

DETAILED DESCRIPTION OF THE INVENTION

Figure 1:
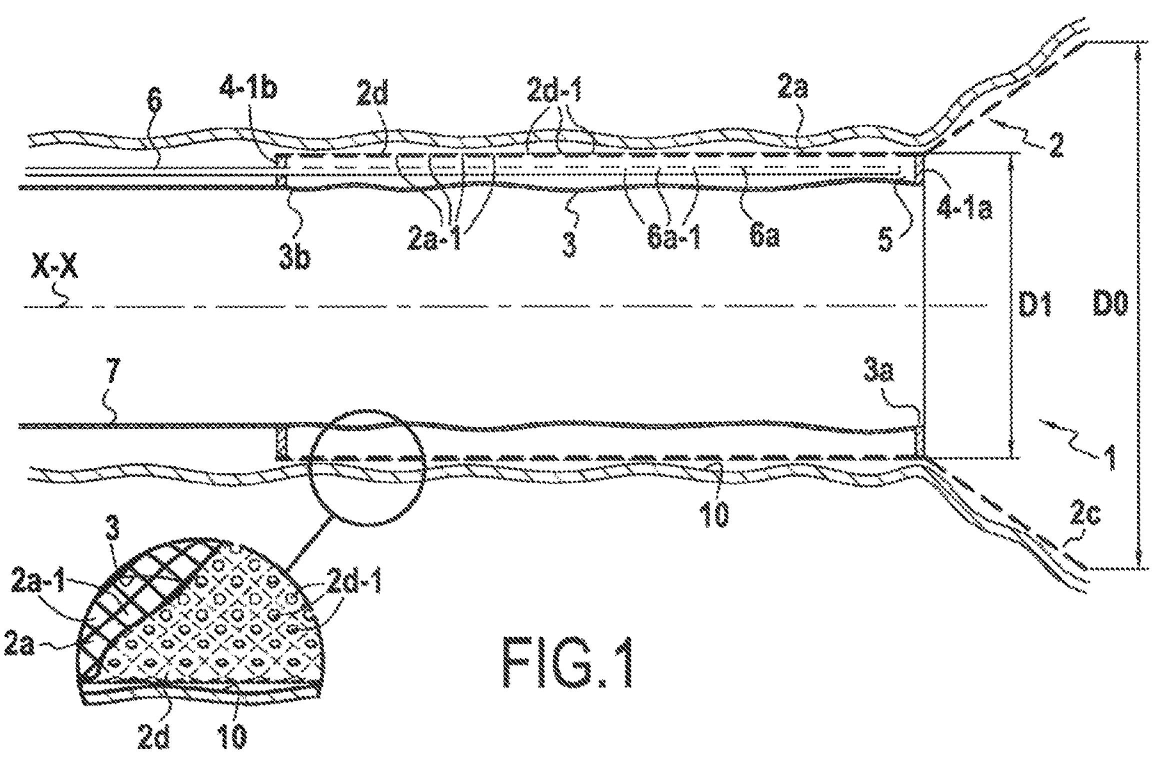
FIG. 1 is a diagrammatic longitudinal section view of a device of the invention comprising a single stent or said first wall and an inner sheath constituted by a flexible leakproof film, said outer sheath being constituted by a flexible film of the same kind extending said inner sheath.

FIG. 1 shows a surgical device 1 for anchoring on the mucous membrane of the inner wall of the intestine 10, the device comprising a temporary anchor element 2 constituted by a first and only semi-rigid hollow longitudinal element defining a wall in the form of a surface of revolution around a longitudinal axis XX having a substantially cylindrical multiply-perforated main portion of substantially circular section referred to as a "first" wall 2*a*, said anchor element 2 being made of a material that gives it properties of radial elasticity so as to enable it to be compressed radially into a retracted position and to adopt a said maximum radially expanded position after the radial compression has been released, whereby said multiply-perforated wall presents a first outer diameter that can be varied in controlled manner between:

- a minimum first outer diameter D1' in said radially retracted position of said first wall, which is preferably no more than 10 mm; and
- a maximum first outer diameter D1 in said maximally radially expanded position of said first wall, preferably lying in the range 18 mm to 45 mm.

Figure 1A:
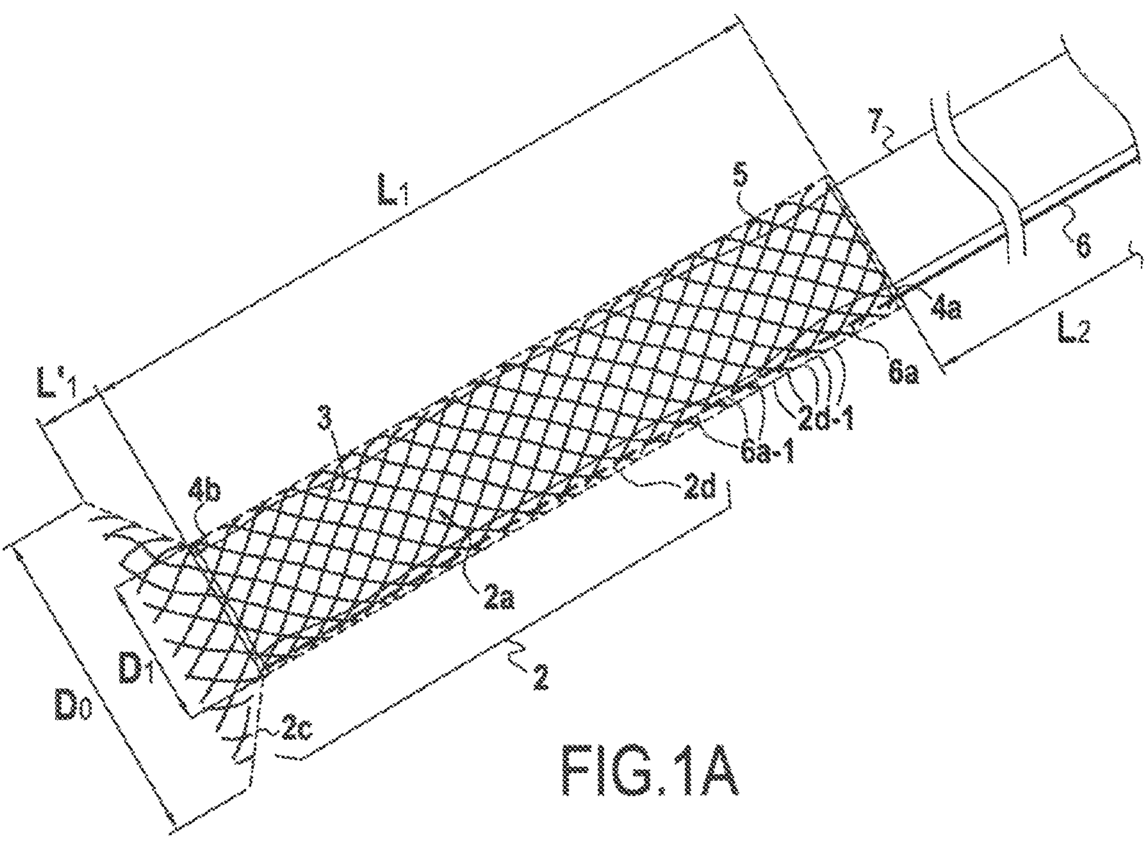
FIG. 1A is a side view of the FIG. 1 device.

Said hollow longitudinal element of said first wall 2*a* is a stent of the type made by a mesh of spiral-wound metal wires made of nitinol, as shown diagrammatically in FIG. 1A, with the anchoring thereof being modifiable in controlled manner as a function of temperature. It presents properties of radial expansion that are controlled as a function of temperature. More precisely, and as a result of the properties of the nitinol, it expands radially in progressive manner as soon as it is placed at a temperature higher than a temperature of about 20° C.

The multiple perforations 2*a*-1 of said first wall 2*a* correspond to the orifices in the mesh made by the spiral-wound mesh of nitinol wires.

The dimensional data concerning the data D1' and D1 as given above corresponds to dimensions that are appropriate for anchoring the device against the mucous membrane of the inner wall of the intestine 10 at various positions between and including the rectum and the esophagus.

In FIG. 1, the stent 2*a* is covered in a layer 2*d* of polyurethane or of silicone, which is itself multiply-perforated at 2*d*-1 on the outer surface of 2*a*. This layer 2*d* protects the intestinal wall 10 by avoiding it becoming incrusted by the outer surface of the stent 2*a*.

The entire length of the cylindrical inner surface of said first wall 2*a* is lined with an independent leakproof layer forming an inner sheath 3, with only the longitudinal ends 3*a*, 3*b* of said inner sheath 3 being fastened in leaktight manner 4*a*, 4*b* to said anchor element 2 with the help of first leaktight fastener means 4-1*a*, 4-1*b* constituting an annular gasket of elastomeric adhesive at each said longitudinal end (3*a*, 3*b*) of said inner sheath.

In FIG. 1, said inner sheath 3 is constituted by a leakproof film forming a flexible tubular wall.

The device of the invention also includes an outer sheath 7 having a tubular wall constituted by a flexible film fastened to said anchor element 2 at one longitudinal end of said anchor element.

In FIG. 1, said outer sheath 7 constitutes an extension of said inner sheath 3 extending over the outside of said anchor element along the longitudinal direction of said anchor element.

The device of the invention also has a flexible or semi-rigid tube referred to as an injection-suction tube 6 that extends outside said anchor element 2.

Said inner sheath 3 is independent of the inner surface of said first wall between these two ends 3 and 3*b*, so it can be understood that the inner sheath 3 is not excessively tensioned in order to avoid stiffening the stent, such that the spacing between said inner sheath 3 and said maximum first outer diameter D1 of the first wall 2*a* preferably lies in the range 0.2 mm to 10 mm, more preferably in the range 1 mm to 5 mm, and the space between said inner sheath 3 and said first wall 2*a* defines a chamber referred to as the "suction" chamber 5. An open end of the injection-suction tube constituted by a portion of tubes 6*a* having multiple perforations 6*a*-1 extends substantially over the entire length of said chamber 5 in the longitudinal direction XX of the device. The injection-suction tube 6 opens out into said suction chamber 5 by passing in leaktight manner through the annular elastomer adhesive gasket at the downstream end 3*b* of the sheath 3 when the tube 6 is inserted via the anal orifice, or the gasket at the upstream end 3*a* of the sheath 3 when the tube 6 is inserted via the oral orifice.

Said injection-suction tube 6 and said outer sheath 7 extend outside said anchor element from the same downstream end of said anchor element, and preferably said injection-suction tube 6 and said outer sheath 7 are stuck together on the outside of said outer sheath 7 for anal insertion.

The injection-suction tube 6 serves to inject or suck air or a liquid into or from the chamber 5 in order to suck the intestinal wall 10 against the outer face of the stent 2*a* or to separate it therefrom, and more generally in order to modify the anchoring characteristic of the stent 2*a* relative to the intestinal wall 10. The layer 2*d* is perforated at 2*d*-1 in order to allow the air or the liquid to pass through.

In FIG. 1, the portion 6*a* of the injection-suction tube 6 inside the chamber 5 may be stuck to the inner face of the first wall 2*a* or to the outer face of said outer sheath.

In all embodiments, said first wall 2*a* presents:

a) a length L1 of at least 30 mm, preferably lying in the range 40 mm to 150 mm, and an outer diameter that may be varied in controlled manner between a minimum outer diameter D1' in the retracted radial position of said first wall of at most 10 mm, and a maximum outer diameter D1 in the maximally radially expanded position of said first wall lying in the range 18 mm to 45 mm, preferably in the range 20 mm to 35 mm; and b) its upstream longitudinal end with a flared extension 2*c* referred to as a "collar", defining a wall in the form of a surface of revolution around said longitudinal axis XX, presenting a section that is circular and of increasing diameter, preferably having a length L1' lying in the range 5 mm to 30 mm, more preferably a length lying in the range 15 mm to 20 mm, with a maximum diameter DO equal to about 110% of said maximum first diameter, and more particularly lying in the range 21 mm to 37 mm.

This collar 2*c* serves to slow down migration of the device 1 inside the intestine even after its anchoring against the inner wall 10 of the intestine has been eliminated in the main longitudinal portion or outer surface of the first wall 2*a*.

In all embodiments, said outer sheath 7 presents, at rest, a length L2 downstream from said anchor element 2 of at least 50 cm, preferably at least 1 m, and an outer diameter lying in the range 18 mm to 45 mm, preferably lying in the range 20 mm to 35 mm.

Figure 2:
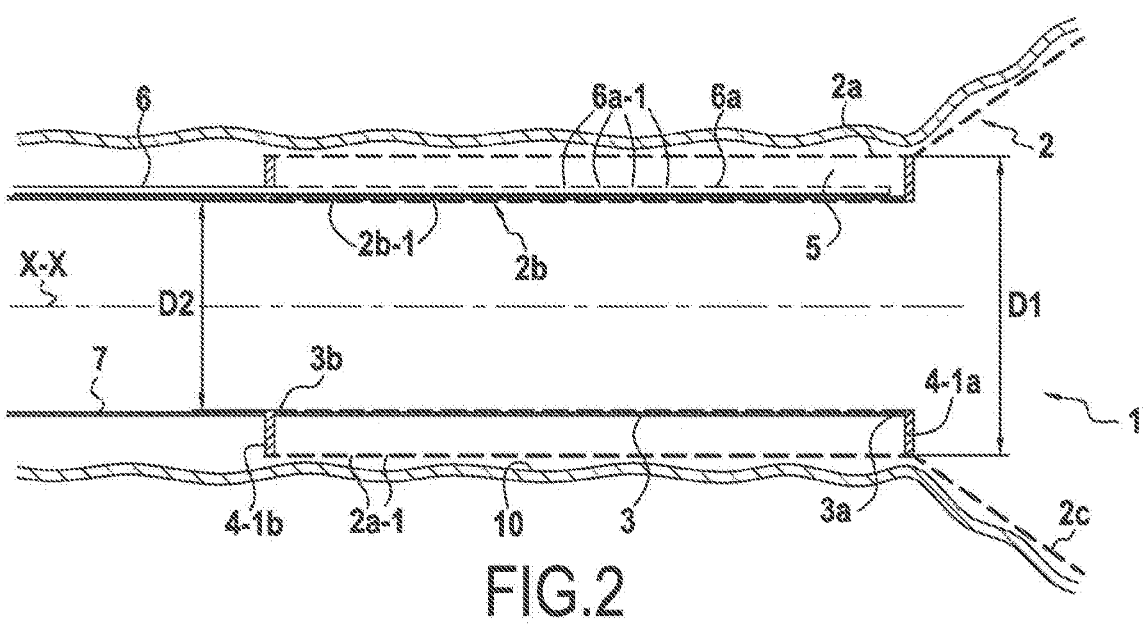
FIG. 2 is a diagram in longitudinal section of a device of the invention in which said inner sheath covers the outer face of a second wall formed by an inner second stent arranged coaxially.

In FIG. 2, the device of the invention includes a second stent 2*b* arranged coaxially inside said first stent 2*a*, said second stent 2*b* being constituted by another small enteral prosthesis formed by a mesh of spiral-wound nitinol wires having its outer surface covered in a leakproof film constituting said inner sheath 3, said second wall 2*b* defining a surface of revolution around said longitudinal axis XX having a main portion that is substantially cylindrical of substantially circular section, said second wall presenting a second outer diameter smaller than said first outer diameter of said first wall 2*a*, the longitudinal ends of said second wall 2*b* being fastened in leaktight manner to the longitudinal ends of said first wall 2*a* by means of first leaktight fastener means 4-1*a*, 4-1*b* constituting an annular elastomer adhesive gasket 4*a*, 4*b* at each said longitudinal end of said second wall, so as to define said leaktight suction chamber 5 laterally, said second hollow cylindrical element being made of a material giving it radial elasticity properties such as to enable it to be compressed radially into said retracted position and to adopt a said maximally radially expanded position after releasing the radial compression in such a manner that said second outer diameter of said second wall 2*b* can vary in controlled manner between:

- a minimum second outer diameter D2' in the radially retracted position of said second wall that is smaller than said minimum first outer diameter;
- a maximum second outer diameter D2 in the maximally radially expanded position of said second wall, that is smaller than said maximum first outer diameter; and
- the spacing between said maximum second outer diameter D2 and said maximum first outer diameter D1 being at least 0.2 mm, preferably lying in the range 0.2 mm to 10 mm, and more preferably lying in the range 1 mm to 5 mm.

In this embodiment of FIG. 2, when air is sucked from the outer end of the injection-suction tube 6, the suction through the perforations 6*a*-1 of the inner tubes portion in the suction chamber 5 causes the intestinal wall 10 to be stuck against the outer surface of the first wall 2*a* via the mesh 2*a*-1. However, the space between the inner sheath 3 and the outer stent 2*a* remains substantially constant, thus making it possible to avoid clogging the perforations 6*a*-1 of the tube portion 6*a* and thus enabling the vacuum level inside the suction chamber 5 to be controlled in more reliable and more uniform manner. This also makes it possible to control the anchor force of the device 1 against the inner wall 10 of the intestine in more reliable and more uniform manner. In the embodiment of FIG. 1, there is a risk of the inner sheath 3 sticking against the perforations 6*a*-1.

In this embodiment of FIG. 2, as in the embodiment of FIG. 1, the injection-suction tube 6 passes through the first fastener means or annular elastomer adhesive gasket 4-1*b* at the downstream end of the anchor element 2.

In FIG. 2, the portion 6*a* of the injection-suction tube 6 inside the chamber 5 may be stuck to the outer face of the inner film or sheath 3 over the outer face of the second wall 2*b*.

Advantageously, the outer sheath 7 is constituted by an extension downstream from the anchor element in the longitudinal direction of said inner sheath 3.

In a variant, the outer sheath 7 may be fastened at its upstream end to the same elastomer adhesive gasket 4-1*b* or it may be fastened to the outer face of the downstream longitudinal end of the first wall 2*a* by overlying it over a short portion of its length (not shown in the figures).

In an embodiment (not shown in the figures), the upstream end of the sheath 7 may also cover the outer surface of the second wall 2*b*, thus constituting said inner sheath 3 or only a portion thereof.

Figure 3:
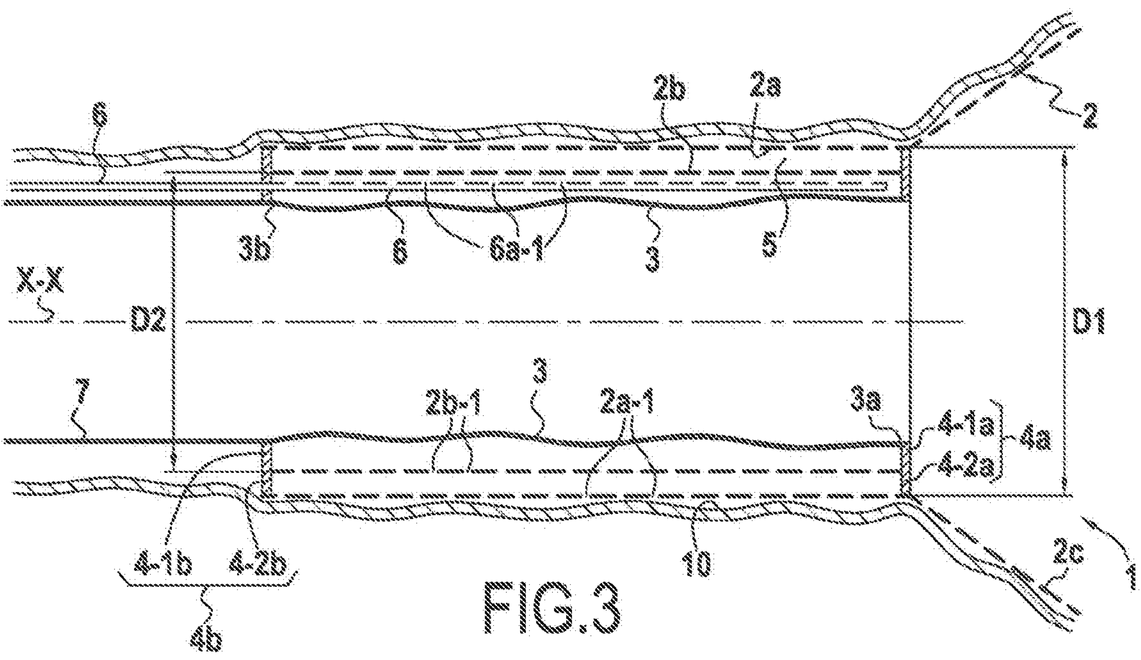
FIG. 3 is a diagram in longitudinal section of a third embodiment of a device of the invention likewise comprising two coaxial stents, said injection-suction tube being interposed between an inner stent constituted by a flexible leakproof film and a said second wall of the inner stent.

FIG. 3 shows a third embodiment in which said inner sheath 3 is applied facing the inner surface of the inner stent or second wall 2*b*, i.e. inside it and stuck against it at its longitudinal ends. This likewise provides a suction chamber 5 presenting substantially permanent radial spacing in the radially expanded position of the first wall 2*a* because use is made of a multiply-perforated second wall 2*b* as in the above-described embodiment of FIG. 2, which wall is constituted by a stent of smaller diameter. The second stent or inner stent 2*b* defines a said second multiply-perforated wall 2*b* interposed between said inner sheath 3 and said first wall 2*a*. The end of said injection-suction tube 6*a* opens out into said suction chamber 5 between said inner sheath 3 and said second wall 2*b*, said inner sheath 3 being constituted by an upstream extension of said outer sheath 7 constituted by a flexible tubular wall, as in FIG. 1.

In the embodiment of FIG. 3, the portion 6*a* of the injection-suction tube 6 that is interposed between the inner sheath 3 and the second wall 2*b* inside the chamber 5 may be stuck against the inner face of the second wall 2*b*. When air is sucked through the openings 6*a*-1 of the tube portion 6*a* in the chamber 5, the flexible sheath 3 is stuck against the tube 6*a* and the intestinal wall 10 is stuck against the outer face of the outer stent 2*a*, but the space between the two coaxial stents 2*a* and 2*b* is kept constant, as described above, with a spacing of at least 0.2 mm to 10 mm, and preferably lying in the range 1 mm to 5 mm, in the radially extended position of said stent. This leads to the same advantage as in the embodiment of FIG. 2 in terms of the ease, the uniformity, and the reliability with which the anchoring of the stent 2*a* relative to the intestinal wall 10 can be controlled.

In the embodiment of FIG. 3, the annular elastomer adhesive gasket 4*a*, 4*b* at each longitudinal end of the main portion of the anchor element 2, i.e. at each longitudinal end 3*a*, 3*b* of the inner sheath 3 and of the first and second walls 2*a* and 2*b*, is constituted by a first annular gasket portion 4-1*a*, 4-1*b* between the sheath 3*c* and the second wall 2*b*, and by a second annular gasket portion 4-2*a*, 4-2*b* between the two coaxial stents constituting the first wall 2*a* and the second wall 2*b*.

Figure 4:
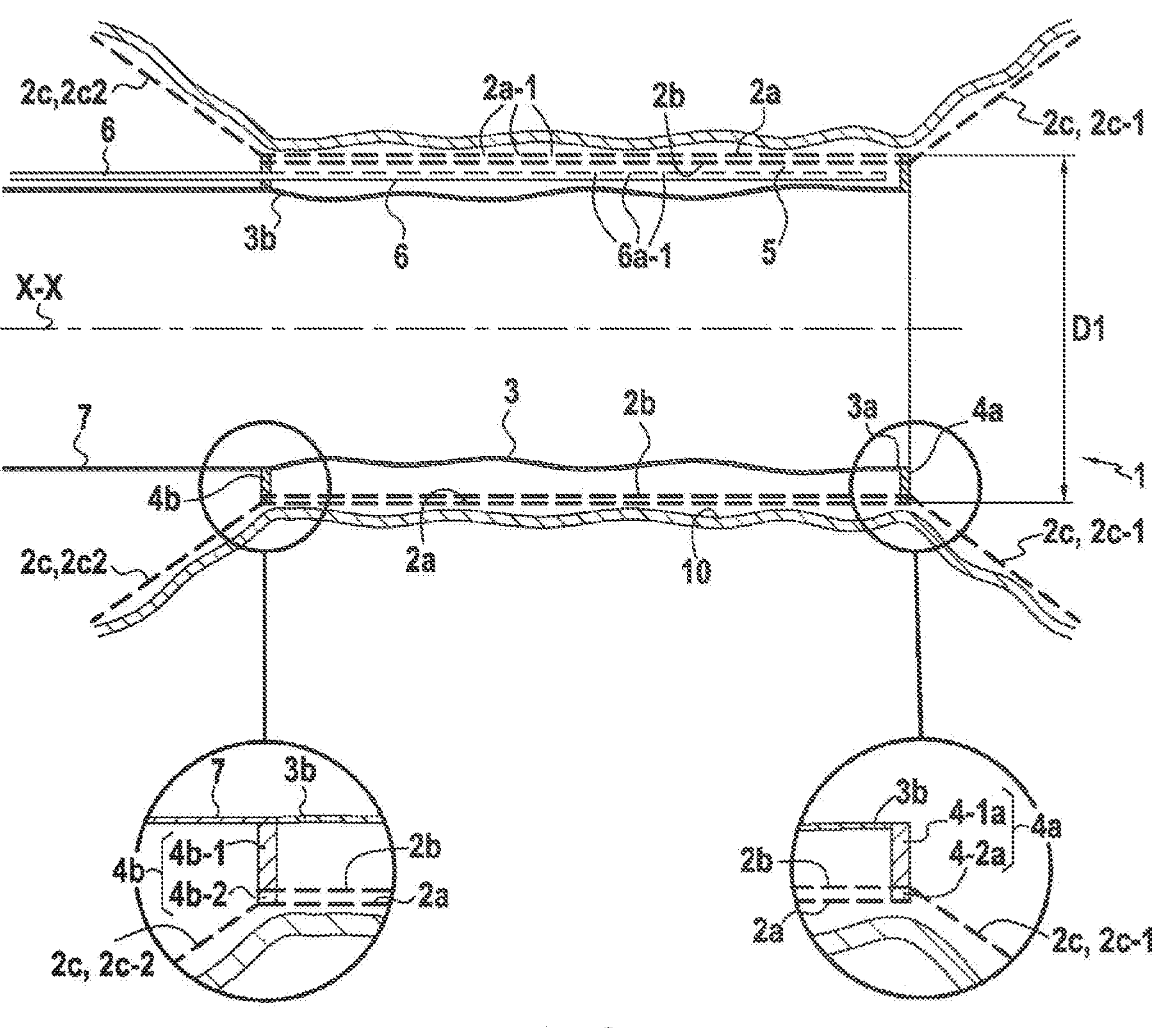
FIG. 4 is a diagram of an embodiment with the anchor element 2 constituted by two coaxial stents at said first and second coaxial walls 2*a*, 2*b*, having a nominal diameter that is the same or substantially identical, and fitted one in (and against) the other.

FIG. 4 shows an embodiment with two coaxial stents of nominal diameters for their main portions that are substantially identical. Each stent has a collar 2*c*, 2*c*-1, 2*c*-2 at one of its longitudinal ends, as described above, and the two stents 2*a*, 2*b* are engaged coaxially one inside the other head to tail so that the anchor element 2 has a collar at each of its longitudinal ends.

The fact that both stents 2*a* and 2*b* present substantially identical nominal diameters, i.e. maximum outer diameters D1 and D2, means that the inner stent 2*b* has its cylindrical main portion constituting said second wall 2*b* engaged as a force-fit against the inner surface of the cylindrical main portion of the first stent or first wall 2*a*. The two stents are stuck one against the other at their longitudinal ends of their said facing cylindrical main portions or first and second walls 2*a*, 2*b*.

As shown in FIG. 3, the inner sheath 3 is pressed against the inside of the inner stent, being stuck to said second wall 2*b*, and the inner sheath 3 thus constitutes the extension of the outer sheath 7.

As in FIG. 3, the injection-suction tube 6 is pressed against the inner surface of the second wall 2*b* between the second wall 2*b* and the inner sheath 3.

More precisely, in FIG. 4, the second wall 2*b* or inner stent presents a collar 2*c*-1 at its upstream end, while the outer stent or first wall 2*a* presents a collar 2*c*-2 at its downstream end, the first and second walls 2*a*, 2*b* overlapping over their entire length.

Thus, because the downstream collar 2*c*-2 extends the outer stent, it is possible to place the injection-suction tube 6 so that it extends downstream from the anchor element 2 so that its open end 6*a* opens out either into the space between the inner sheath 3 and the second wall 2*b* of the inner stent, as shown in FIG. 4, or else in a variant that is not shown, with the open end of the injection-suction tube 6 opening out into the space between the two stents. More precisely, the portion 6*a* of the tube 6 may be interposed between the first and second walls 2*a*, 2*b*, i.e. it may be stuck against the outer face of the second wall 2*b*.

This FIG. 4 embodiment preserves sufficient space between the inner sheath and the intestinal wall 10, thus avoiding clogging of the perforations 6*a* in the end of the injection-suction tube 6. In addition, it imparts optimum stiffness to the anchor element 2 and provides stabilization of sufficient length in the intestinal wall before migrating after the digestive process has restarted.

Figure 5:
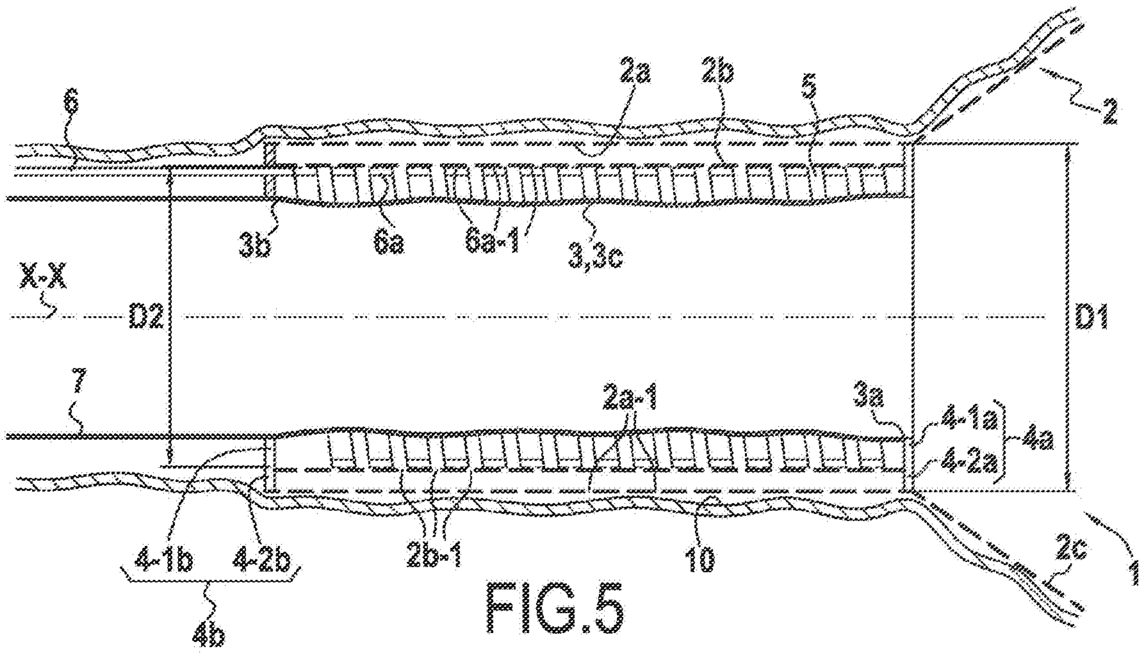
FIG. 5 is a longitudinal section view of a device of the invention as shown in FIG. 3, including a multiply-perforated injection-suction tube as shown in FIG. 5A.
Figure 5A:
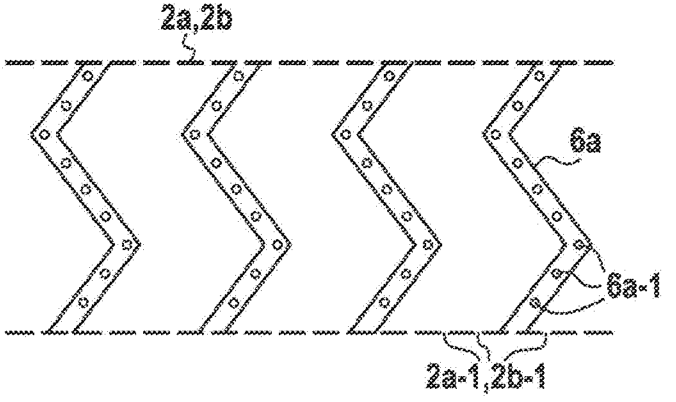
FIG. 5A is a diagrammatic side view in longitudinal section of an embodiment of the end of the injection-suction tube constituted by a portion of multiply-perforated tubes extending in a Z-shape running along the suction chamber substantially helically against a face of said first wall or of said second wall of a stent of the anchor element.

FIG. 5A is a diagram showing an embodiment of the end of the injection-suction tube 6 constituted by a tube portion 6*a* having multiple perforations 6*a*-1, the tube portion extending substantially helically against the inner face of said second wall 2*b*, as shown in FIG. 5, following a zigzag or a Z-shaped line and running along the entire length of the suction chamber 5. This type of zigzag tube is pressed against the inner face of the second wall 2*b* and is stuck thereto.

The zigzag or Z-shaped multiply-perforated tube portion 6*a* within the chamber 5 may also be pressed against and stuck to the inner surface of the second wall 2*a* or the outer surface of the second wall 2*b* in the embodiment of FIG. 2, by making it run helically lengthwise in the direction XX of the annular chamber 5.

Three other variants of the device that are not shown are possible:

1) a stent 2*a* with two collars and a stent 2*b* without a collar;
2) a stent 2*a* without a collar and a stent 2*b* with only one collar; and
3) a stent 2*a* without a collar and a stent 2*b* with two collars.

Figure 6:
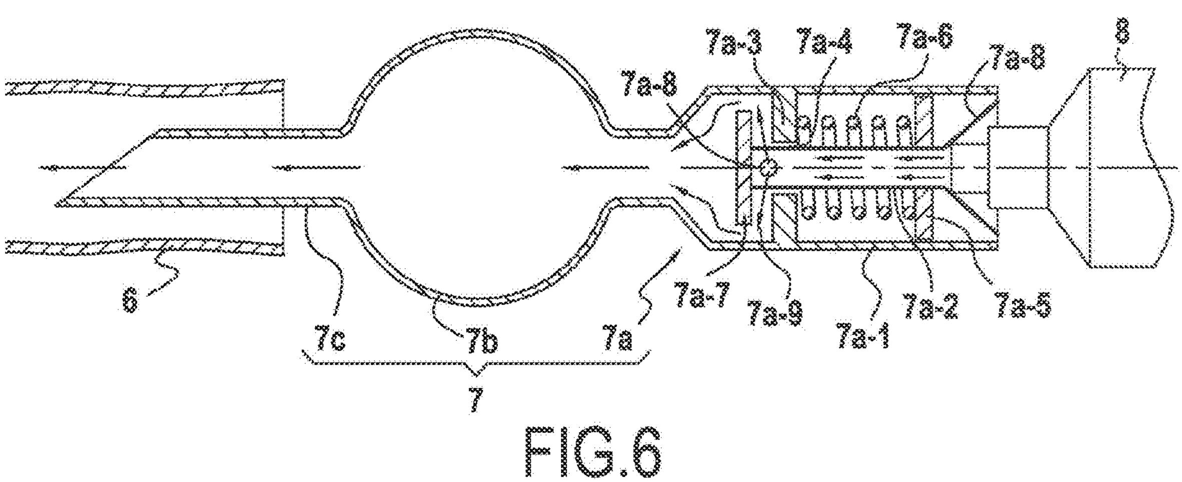
FIG. 6 shows a device of the invention fitted with a connection endpiece 7 co-operating with a syringe 8, said endpiece 7 including an anti-reflux valve 7*a* and a balloon 7*b* having a connection rod 7*c* and suitable for being pushed into the end of the injection-suction tube 6.

FIG. 6 shows the outer free longitudinal end of said injection-suction tube 6 reversibly connected to a connection endpiece 7 including a shutter device consisting in an anti-reflux valve 7*a*, and including an indicator device for indicating the degree of vacuum in the chamber 5, which device is constituted by a balloon 7*b*.

More precisely, the connection endpiece 7 comprises a rigid connection rod 7*c* extended by said indicator balloon 7*b* itself co-operating with and extended by the anti-reflux device 7*a*.

The connection endpiece 7 may be connected to a suction appliance, e.g. a syringe 8 at the free end of the anti-reflux device 7*a*. A connection endpiece 7 of this type is sold by the supplier Teleflex Medical Company (USA) under the reference Ruschlit PVC No. 1039020353.

The anti-reflux device 7*a* comprises an outer hollow cylinder 7*a*-1 and an inner hollow central cylinder 7*a*-2. The hollow central cylinder 7*a*-2 is guided inside the outer cylinder 7*a*-1 by a first abutment 7*a*-3 secured to the inner wall of the outer cylinder 7*a*-1 and including a central orifice 7*a*-4 through which said hollow central cylinder 7*a*-2 passes. A second abutment 7*a*-5 is secured to said hollow central cylinder 7*a*-2, and a spring 7*a*-6 is secured by respective ends to said first abutment 7*a*-3 and to said second abutment 7*a*-5 so that in the extended position of said spring, a third abutment 7*a*-7 secured to the other end of said hollow central cylinder 7*a*-1 comes into abutment against a face of the first abutment 7*a*-3. When the end of the syringe 8 is fitted in the flared end 7*a*-8 of said hollow central cylinder 7*a*-1, the bearing force of the syringe serves to compress the spring and separate said first and third abutments 7*a*-3 and 7*a*-7 so that the air injected by the syringe 8 can flow from an orifice 7*a*-8 at the end of said hollow central cylinder via the passage 7*a*-9 between said first and third abutments 7*a*-3 and 7*a*-7. After the syringe 8 has been removed, the spring 7*a*-6 returns to its extended position and the third abutment 7*a*-7 comes to press against the first abutment 7*a*-3 and shut off any passage for air between the outside of the anti-reflux device 7*a* and the inside of the balloon 7*b*.

By sucking air into the perforated mini-tube 6*a* using the syringe 8 via the connection endpiece 7, a vacuum is created in the suction chamber 5. The intestinal mucous membrane 10 is attracted to the outer surface of the stent 2*a* under the effect of the suction, thereby increasing the anchoring of the device 1. Conversely, this effect is canceled by injecting air or a liquid solution into said suction chamber 5 using the same mini-tube 6 from the outer free longitudinal end of the injection-suction tube 6.

As mentioned above, when a liquid solution is injected into the suction chamber 5, the temperature of the solution can be used to modify the temperature and thus the shape and the stiffness of the first wall 2*a*, which is made of nitinol alloy. More particularly, at temperatures lower than 15° C., nitinol becomes flexible and malleable, such that introducing a cold liquid in the range 0° C. to 15° C. in the chamber 5 can make the stent 2*a* malleable, and possibly also the stent 2*b*, thereby facilitating migration of the stent on passing through the anastomosis or through a zone of narrowing, for example.

The flexible sheaths 3 or 7 may be made using a mixture of various types of silicone, e.g. of the LSR, RTV, and gel types, as described above.

WO 2010/092291 describes introducing the device of the invention. It is introduced while in retracted form by means of an introducer 4 that is constituted by a semi-rigid plastics tube suitable for being deformed and having a diameter lying in the range 3 mm to 20 mm, preferably in the range 10 mm to 15 mm, and a length lying in the range 70 cm to 220 cm, with the anchor element being inserted therein in its retracted shape, said sheath being positioned downstream from the anchor element inside the guide tube of the introducer. Once the guide tube of the introducer has reached the implantation site, e.g. about 1 m upstream from the anastomosis, the anchor element may be moved out from the end of the introducer and it may take up an expanded position. It should be observed that the time required for introducing and moving the anchor element introducer to the implantation site is in practice shorter than the time after which said anchor element is subjected to radial expansion as a result of its temperature increasing because it is inside the body.

In its initial shape, in which it is closed and housed inside the introducer, the stent(s) 2*a*, 2*b* present(s) a diameter that is very small, in particular lying in the range 5 mm to 15 mm. It is passed through the anastomosis, and then into the upstream intestine. The surgeon assesses progress of the introducer and whether it is properly positioned by palpating the introducer through the walls of the intestine and viewing the stent during its expansion. Once released in the lumen of the intestine, the stent progressively returns to its final diameter. It can be held temporarily in place by the surgeon pinching the stent through the walls of the intestine. The introducer is then withdrawn. The sheath 7 unfolds spontaneously and progressively as the introducer is withdrawn. The introducer passes back through the anastomosis and then through the anal orifice in the reverse direction, thereby completely releasing the sheath 7. After an average period of four days to six days, and under the effect of intestinal contractions, the unit comprising the stent, the outer sheath, and the injection-suction tube migrates progressively towards the anal orifice from its upstream anchor site, which site is far enough upstream from the anastomosis, preferably via at least 20 cm of intestine length, to ensure that the stent reaches the anal orifice five or six days later, only after the digestive process has restarted, after which the device is eliminated with fecal matter.

The device of the invention may be combined with other means for a purpose other than protecting an anastomosis.

In particular, it may be used for all applications requiring anchoring in the intestine, in particular for the purpose of controlling such anchoring better.

Mention is made in particular of devices for increasing the sensation of being sated, as described in US 2008/0208357.

What is claimed:

1. An anchoring device for protecting an anastomosis in an intestine during healing, the anchoring device comprising:

an anchor configured to be implanted in the intestine at an anchor site upstream of the anastomosis in the intestine, wherein the anchor comprises an expandable downstream region and an expandable upstream region each configured to expand to a diameter greater than that of a cylindrical region therebetween to inhibit migration of the anchor from the anchor site, wherein the anchor is configured to define a suction chamber;

a covering at the anchor configured to promote adhesion to an inner wall of the intestine at the anchor site while the anchor is implanted; and a tube in fluid connection with the suction chamber, wherein negative pressure applied to the suction chamber via the tube creates a vacuum in the suction chamber to anchor the anchor in the intestine at the anchor site upstream of the anastomosis, wherein the anchor is configured to remain anchored against the inner wall of the intestine at the anchor site during a period that is after post-operative restarting of a digestive process to allow for healing of the anastomosis while the anchor remains implanted in the intestine.

2. The anchoring device of claim 1, wherein the covering comprises a covering film having adhesive properties.

3. The anchoring device of claim 1, wherein the covering creates a textured outer surface on the anchor.

4. The anchoring device of claim 3, wherein the textured outer surface comprises micro-fibrils.

5. The anchoring device of claim 1, wherein the covering comprises a biocompatible synthetic material.

6. The anchoring device of claim 5, wherein the biocompatible synthetic material comprises an elastomer.

7. The anchoring device of claim 6, wherein the elastomer comprises at least one of silicone or polyurethane.

8. The anchoring device of claim 1, wherein the covering is configured to protect the inner wall of the intestine during implantation.

9. The anchoring device of claim 1, wherein the anchor comprises two stents configured to be secured together.

10. The anchoring device of claim 1, wherein the anchor comprises pores or mini-perforations.

11. The anchoring device of claim 1, wherein the anchor is configured to be implanted in the intestine for at least three days until removal.

12. The anchoring device of claim 1, further comprising an external suction device configured to create the vacuum in the suction chamber via the tube.

13. The anchoring device of claim 12, further comprising a vacuum indicator configured to indicate a degree of vacuum in the suction chamber.

14. The anchoring device of claim 13, wherein the external suction device is configured to, responsive to the indication of the degree of vacuum from the vacuum indicator, permit monitoring and control or modification of anchor force of the anchor against the inner wall of the intestine.

15. The anchoring device of claim 1, further comprising a sheath defining a lumen, wherein the sheath extends downstream from the anchor to cover and protect the anastomosis in the intestine from fecal matter flowing through the lumen.

16. The anchoring device of claim 15, wherein the sheath has a length to extend downstream from the anchor to outside an anal orifice.

17. The anchoring device of claim 15, wherein the covering has a flexibility that is greater than a flexibility of the sheath.

18. The anchoring device of claim 1, further comprising an additional tube for creating the vacuum in the suction chamber.

19. The anchoring device of claim 1, further comprising a first leaktight fastener disposed on an upstream end of the anchor and a second leaktight fastener disposed on a downstream end of the anchor.

20. The anchoring device of claim 19, wherein the first and second leaktight fasteners each form a leaktight sealed configuration with the inner wall of the intestine at the anchor site positioned upstream from the anastomosis.

21. The anchoring device of claim 20, wherein the first and second leaktight fasteners comprise first and second annular gaskets, respectively.

22. The anchoring device of claim 1, wherein the anchor is configured to be removed using a coloscope.

23. The anchoring device of claim 1, wherein the suction chamber is configured to receive gas or liquid via the tube to release the anchor from the anchor site for removal from the intestine via an anal orifice after healing of the anastomosis.

24. The anchoring device of claim 1, wherein the suction chamber is between the expandable downstream region and the expandable upstream region of the anchor.

25. A delivery system comprising:

a tubular outer shell configured to hold the anchoring device of claim 1 in a retracted position; and a pusher tube within the tubular outer shell, wherein the anchoring device is configured to be introduced into the intestine via an anal orifice and pushed out the tubular outer shell via the pusher tube for anchoring the anchor in the intestine upstream of the anastomosis.

* * * * *